United States Patent [19]
Sakurai et al.

[11] Patent Number: 5,464,942
[45] Date of Patent: Nov. 7, 1995

[54] PHOSPHOLIPID- OR LIPID-LINKED GLYCOSAMINOGLYCAN AND PROCESS FOR PRODUCING THE SAME

[75] Inventors: Katsukiyo Sakurai, Tokyo; Nobuo Sugiura, Gifu; Koji Kimata; Sakaru Suzuki, both of Aichi, all of Japan

[73] Assignee: Seikagaku Kogyo Kabushiki Kaisha, Tokyo, Japan

[21] Appl. No.: 847,065

[22] PCT Filed: Jul. 24, 1991

[86] PCT No.: PCT/JP91/00995

§ 371 Date: Mar. 24, 1992

§ 102(e) Date: Mar. 24, 1992

[87] PCT Pub. No.: WO92/01720

PCT Pub. Date: Feb. 6, 1992

[30] Foreign Application Priority Data

Jul. 24, 1990 [JP] Japan ..................................... 2-193816
Jul. 24, 1990 [JP] Japan ..................................... 2-193817
Jul. 24, 1990 [JP] Japan ..................................... 2-193818

[51] Int. Cl.$^6$ .......................... A61K 31/725; C08B 37/10
[52] U.S. Cl. .................... 536/21; 536/4.1; 536/17.1; 536/17.2; 536/53; 536/54; 536/55; 536/55.1; 536/55.3; 536/117; 536/123
[58] Field of Search ........................ 514/54, 56; 536/4.1, 536/17.1, 17.2, 53, 54, 55, 21, 55.1, 55.3, 117, 123

[56] References Cited

U.S. PATENT DOCUMENTS

| | | | |
|---|---|---|---|
| 4,239,754 | 12/1980 | Sache et al. ................. | 514/56 |
| 4,362,737 | 12/1982 | Schafer et al. .............. | 514/56 |
| 4,604,376 | 8/1986 | Teng ........................... | 514/56 |
| 4,654,327 | 3/1987 | Teng ........................... | 514/56 |
| 4,882,318 | 11/1989 | Vlodansky et al. ........... | 514/56 |
| 5,118,671 | 6/1992 | Bombardelli et al. ........ | 536/4.1 |
| 5,120,719 | 6/1992 | Iwamoto et al. ............. | 536/4.1 |
| 5,169,636 | 12/1992 | Nanba et al. ................ | 536/4.1 |

FOREIGN PATENT DOCUMENTS

| | | |
|---|---|---|
| 0114589 | 8/1984 | European Pat. Off. . |
| 0198388 | 10/1986 | European Pat. Off. . |
| 2492259 | 4/1982 | France . |
| 397650 | 5/1939 | Japan . |
| 6117 | 1/1986 | Japan . |
| 219393 | 1/1990 | Japan . |
| 258501 | 2/1990 | Japan . |
| 8702777 | 5/1987 | WIPO . |

OTHER PUBLICATIONS

Tsubura et al; Cancer Invasion and Metastasis: Biolog. Mech & Ther. 367–381 (1977).
Vannucchi et al; Biochem. J. 227:57–65 (1985).
Coombe et al; Int. J. Cancer 39(1):82–8 (1987).
Parish et al; Int. J. Cancer 40:511–8 (1987).
Hall et al; Biomaterials 10(4):219–224 (1989).
Kim et al; Thromb. Res. 56:369–376 (1989).
Lee et al; Chemical Abstracts 113:17566p (1990).
Soeda et al; Biochemistry 29:5188–94 (May 29, 1990).

*Primary Examiner*—Douglas W. Robinson
*Assistant Examiner*—Kathleeen Kahler Fonda
*Attorney, Agent, or Firm*—Sughrue, Mion, Zinn, Macpeak & Seas

[57] ABSTRACT

This invention relates to compounds prepared by linking glycosaminoglycan to phospholipid or lipid, which are expected to exert a pharmacological effect for inhibiting metastasis because of their excellent function to inhibit adhesion of cancer cells to blood vessel endothelial cells and extracellular matrix. This phospholipid- or lipid-linked glycosaminoglycan can be produced for example by: cleaving and oxidizing reducing terminal group of glycosaminoglycan, and allowing an aldehyde group or a lactone compound of the thus-formed derivative or a carboxyl group in the glycosaminoglycan chain to react with a primary amino group of a phospholipid; or linking a glycosaminoglycan derivative to a phospholipid or a lipid by allowing a primary amino group of the derivative to react with a carboxyl group of the phospholipid or lipid. This phospholipid- or lipid-linked glycosaminoglycan is useful as a metastasis inhibitor because it has no toxicity.

17 Claims, 6 Drawing Sheets

PHOSPHOLIPID- OR LIPID-LINKED GLYCOSAMINOGLYCAN AND PROCESS FOR PRODUCING THE SAME

FIELD OF THE INVENTION

This invention relates to phospholipid- or lipid-linked glycosaminoglycans, a process for producing the same and metastasis inhibitors.

BACKGROUND OF THE INVENTION

During the process of metastasis development, it is known that a cancer cell which has strayed into a blood vessel or lymphoduct adheres to an endothelial cell or to its extracellular matrix (so-called basement membrane) and the thus adhered cancer cell permeates into the extra-cellular matrix to develop a new metastatic lesion in the tissue. For example, S. Korach et al. (*Cancer Research*, 46, 3624–3629, 1986) reported that they have divided cancer cells into a high metastatic group and a low metastatic group and through their cancer cell cloning studies, conducted in vitro adhesion tests of cancer cells to cultured endothelial. As a result, the adhesiveness of cancer cells to blood vessel endothelial cells or to their extra-cellular matrices is closely related to metastasis of cancer cells because the high metastatic group cancer cells showed a high adhesiveness while the low metastatic cells showed a low adhesiveness.

On the other hand, the peptide sequence GRGDS (Gly-Arg-Gly-Asp-Ser) of the cell adhesion moiety of fibronectin which is a component of the extra-cellular matrix, competitively inhibits binding between cancer cells and the extra-cellular matrix. Yamada et al. (*Science*, 233, 467–470, 1986) reported that the peptide GRGDS inhibited lung metastasis of B16F10 cells in mice. These results indicate that a substance which has cell adhesion inhibitory activity in a small amount could be used as a metastasis inhibitor.

The present invention has been accomplished based on a finding that certain types of phospholipid- or lipid-linked glycosaminoglycans can inhibit adhesion of cancer cells to blood vessel endothelial cells and their extra-cellular matrices and, as a result, can inhibit metastasis of cancer cells.

DESCRIPTION OF THE INVENTION

The present invention relates to phospholipid- or lipid-linked glycosaminoglycans, a process for producing the same and metastasis inhibitors containing the same or the salts thereof.

As shown in Table 1, glycosaminoglycan is a long chain polysaccharide which consists of recurring units of disaccharides or tetrasaccharides including D-glucosamine or D-galactosamine, D-glucuronic acid, L-iduronic acid and/or D-galactose. Examples of known glycosaminoglycan include hyaluronic acid, chondroitin, chondroitin sulfate A, chondroitin sulfate C, chondroitin sulfate D, chondroitin sulfate E, chondroitin sulfate K, chondroitin polysulfate, dermatan sulfate, heparin, heparan sulfate, keratan sulfate and keratan polysulfate.

TABLE 1

| Glycosaminoglycan | Hexosamine | Uronic acid |
| --- | --- | --- |
| Hyaluronic acid (MW, 1,000–10,000,000) | GlcNAc | GlcUA |
| Chondroitin (MW, 1,000–100,000) | GalNAc | GlcUA |
| Chondroitin sulfate A (MW, 1,000–100,000) | GalNAc (4S) | GlcUA |
| Chondroitin sulfate C (MW, 1,000–100,000) | GalNAc (6S) | GlcUA |
| Chondroitin sulfate D (MW, 1,000–100,000) | GalNAc (6S) | GlcUA (2S) |
| Chondroitin sulfate E (MW, 1,000–100,000) | GalNAc (4S,6S) | GlcUA |
| Chondroitin sulfate K (MW, 1,000–100,000) | GalNAc (4S) | GlcUA (3S) |
| Chondroitin polysulfate (MW, 1,000–150,000) | GalNAc (S) | GlcUA (S) |
| Dermatan sulfate (MW, 1,000–20,000) | GalNAc (4S) | IduUA, GlcUA |
| Heparin (MW, 1,000–20,000) | GlcNS (6S) | GlcUA, IduUA (2S) |
| Heparan sulfate (MW, 1,000–20,000) | GlcNS (NAc,S) | GlcUA, IduUA (2S) |
| Keratan sulfate (MW, 1,000–20,000) | GlcNAc (6S) | Gal |
| Keratan polysulfate (MW, 1,000–20,000) | GlcNAc (6S) | Gal (6S) |

GlcNAc: N-acetyl-D-glucosamine
GalNAc: N-acetyl-D-galactosamine
GlcNS: D-glucosamine N-sulfate
GlcUA: D-glucuronic acid
IduUA: L-iduronic acid
Gal: D-galactose
S: O-sulfate The phospholipid- or lipid-linked glycosaminoglycan of the present invention can be used as a salt, preferably with an alkali metal such as sodium, potassium or the like, an alkaline earth metal such as calcium, magnesium or the like and an amine such as trialkylamine, pyridine or the like.

The following are examples of the phospholipid- or lipid-linked glycosaminoglycans of the present invention.

A phospholipid-linked glycosaminoglycan represented by the following formula or a salt thereof:

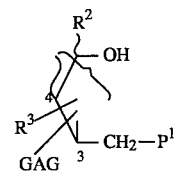
(I)

wherein $p^1$ is a phospholipid having a primary amino group and;

(1) GAG is located at the 4-position, $R^3$ is located at the 3-position, $R^2$ is a COOH group and $R^3$ is an OH group when GAG is a glycosaminoglycan residue of hyaluronic acid, chondroitin, chondroitin sulfate A, C or E, dermatan sulfate or heparin excluding a reducing terminal glucuronic acid moiety or when GAG is a glycosaminoglycan residue of dermatan sulfate excluding a reducing terminal iduronic acid moiety, (2) GAG is located at the 4-position, $R^3$ is located at the 3-position, $R^2$ is a COOH group and $R^3$ is an $OSO_3H$ group when GAG is a glycosaminoglycan residue of chondroitin sulfate K or chondroitin polysulfate excluding a reducing terminal glucuronic acid moiety, (3) GAG is located at the 3-position, $R^3$ is located at the 4-position, $R^2$ is a $CH_2OH$ group and $R^3$ is an OH group when GAG is a glycosaminoglycan residue of keratan sulfate excluding a reducing terminal galactose moiety, and (4) GAG is located at the 3-position, $R^3$ is located at the 4-position, $R^2$ is a $CH_2OSO_3H$ group and $R^3$ is an OH group when GAG is a glycosaminoglycan residue of keratan polysulfate excluding a reducing terminal galactose moiety.

A phospholipid-linked glycosaminoglycan represented by the following formula or a salt thereof:

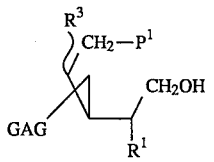

(II)

wherein $p^1$ is a phospholipid having a primary amino group and;

(1) $R^1$ is a $NHCOCH_3$ group and $R^3$ is an OH group when GAG is a glycosaminoglycan residue of hyaluronic acid or chondroitin excluding a reducing terminal hexosamine moiety, (2) $R^1$ is a $NHCOCH_3$ group and $R^3$ is an $OSO_3H$ group when GAG is a glycosaminoglycan residue of chondroitin sulfate A or K, chondroitin polysulfate or dermatan sulfate excluding a reducing terminal hexosamine moiety, and (3) each of $R^1$ and $R^3$ is an OH group when GAG is a glycosaminoglycan residue of keratan sulfate or keratan polysulfate excluding a reducing terminal galactose moiety.

A phospholipid-linked glycosaminoglycan represented by the following formula or a salt thereof:

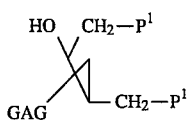

(III)

wherein $p^1$ is a phospholipid having a primary amino group and GAG is a glycosaminoglycan residue of keratan sulfate or keratan polysulfate excluding a reducing terminal galactose moiety.

A phospholipid-linked glycosaminoglycan represented by the following formula or a salt thereof:

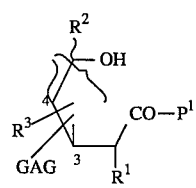

(IV)

wherein $p^1$ is a phospholipid having a primary amino group and;

(1) GAG is located at the 4-position, $R^3$ is located at the 3-position, $R^1$ is an OH group, $R^2$ is a COOH group and $R^3$ is an OH group when GAG is a glycosaminoglycan residue of hyaluronic acid, chondroitin, chondroitin sulfate A, C or E, dermatan sulfate, heparin or heparan sulfate excluding a reducing terminal glucuronic acid moiety or when GAG is a glycosaminoglycan residue of dermatan sulfate excluding a reducing terminal iduronic acid moiety, (2) GAG is located at the 4-position, $R^3$ is located at the 3-position, $R^1$ is an $OSO_3H$ group, $R^2$ is a COOH group and $R^3$ is an OH group when GAG is a glycosaminoglycan residue of chondroitin sulfate D excluding a reducing terminal glucuronic acid moiety or when GAG is a glycosaminoglycan residue of heparin or heparan sulfate excluding a reducing terminal iduronic acid moiety, (3) GAG is located at the 4-position, $R^3$ is located at the 3-position, $R^1$ is an OH group, $R^2$ is a COOH group and $R^3$ is an $OSO_3H$ group when GAG is a glycosaminoglycan residue of chondroitin sulfate K excluding a reducing terminal glucuronic acid moiety, (4) GAG is located at the 4-position, $R^3$ is located at the 3-position, at least one of $R^1$ and $R^3$ is an $OSO_3H$ group, while the other is an OH group, and $R^2$ is a COOH group when GAG is a glycosaminoglycan residue of chondroitin polysulfate excluding a reducing terminal glucuronic acid moiety, (5) GAG is located at the 3-position, $R^3$ is located at the 4-position, each of $R^1$ and $R^3$ is an OH group and $R^2$ is a $CH_2OH$ group when GAG is a glycosaminoglycan residue of keratan sulfate excluding a reducing terminal galactose moiety, (6) GAG is located at the 3-position, $R^3$ is located at the 4-position, each of $R^1$ and $R^3$ is an OH group and $R^2$ is a $CH_2OSO_3H$ group when GAG is a glycosaminoglycan residue of keratan polysulfate excluding a reducing terminal galactose moiety, (7) GAG is located at the 3-position, $R^3$ is located at the 4-position, $R^1$ is an $NHCOCH_3$ group, $R^2$ is a $CH_2OH$ group and $R^3$ is an OH group when GAG is a glycosaminoglycan residue of hyaluronic acid or chondroitin excluding a reducing terminal hexosamine moiety, (8) GAG is located at the 3-position, $R^3$ is located at the 4-position, $R^1$ is an $NHCOCH_3$ group, $R^2$ is a $CH_2OH$ group and $R^3$ is an $OSO_3H$ group when GAG is a glycosaminoglycan residue of chondroitin sulfate A or K or dermatan sulfate excluding a reducing terminal hexosamine moiety, (9) GAG is located at the 3-position, $R^3$ is located at the 4-position, $R^1$ is an $NHCOCH_3$ group, $R^2$ is a $CH_2OSO_3H$ group and $R^3$ is an OH group when GAG is a glycosaminoglycan residue of chondroitin sulfate C or D excluding a reducing terminal hexosamine moiety,

(10) GAG is located at the 3-position, $R^3$ is located at the 4-position, $R^1$ is an $NHCOCH_3$ group, $R^2$ is a $CH_2OSO_3H$ group and $R^3$ is an $OSO_3H$ group when GAG is a glycosaminoglycan residue of chondroitin sulfate E excluding a reducing terminal hexosamine moiety,

(11) GAG is located at the 3-position, $R^3$ is located at the 4-position, $R^1$ is an $NHCOCH_3$ group, $R^2$ is a $CH_2OH$ group and $R^3$ is an $OSO_3H$ group, or $R^2$ is a $CH_2OSO_3H$ group and $R^3$ is an OH group or an $OSO_3H$ group, when GAG is a glycosaminoglycan residue of chondroitin polysulfate excluding a reducing terminal hexosamine moiety,

(12) GAG is located at the 4-position, $R^3$ is located at the 3-position, $R^1$ is an $NHSO_3H$ group, $R^2$ is a $CH_2OSO_3H$ group and $R^3$ is an OH group when GAG is a glycosaminoglycan residue of heparin excluding a reducing terminal hexosamine moiety,

(13) GAG is located at the 4-position, $R^3$ is located at the 3-position, $R^1$ is an $NHCOCH_3$ group or an $NHSO_3H$ group, $R^2$ is a $CH_2OH$ group when $R^3$ is an $OSO_3H$ group, or $R^2$ is a $CH_2OSO_3H$ group when $R^3$ is an OH group or an $OSO_3H$ group, when GAG is a glycosaminoglycan residue of heparan sulfate excluding a reducing terminal hexosamine moiety,

(14) GAG is located at the 4-position, $R^3$ is located at the 3-position, $R^1$ is an $NHCOCH_3$ group, $R^2$ is a $CH_2OSO_3H$ group and $R^3$ is an OH group when GAG is a glycosaminoglycan residue of keratan sulfate or keratan polysulfate excluding a reducing terminal hexosamine moiety.

A phospholipid- or lipid-linked glycosaminoglycan represented by the following formula or a salt thereof:

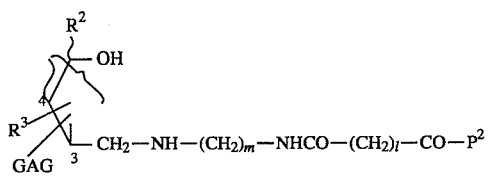
(V)

wherein $p^2$ is a phospholipid or a lipid, m is an integer of 1 to 8 and l is an integer of 1 to 10, and;

(1) GAG is located at the 4-position, $R^3$ is located at the 3-position, $R^2$ is a COOH group and $R^3$ is an OH group when GAG is a glycosaminoglycan residue of hyaluronic acid, chondroitin, chondroitin sulfate A, C or E, dermatan sulfate, heparin or heparan sulfate excluding a reducing terminal glucuronic acid moiety or when GAG is a glycosaminoglycan residue of dermatan sulfate excluding a reducing terminal iduronic acid moiety, (2) GAG is located at the 4-position, $R^3$ is located at the 3-position, $R^2$ is a COOH group and $R^3$ is an $OSO_3H$ group when GAG is a glycosaminoglycan residue of chondroitin sulfate K or chondroitin polysulfate excluding a reducing terminal glucuronic acid moiety, (3) GAG is located at the 3-position, $R^3$ is located at the 4-position, $R^2$ is a $CH_2OH$ group and $R^3$ is an OH group when GAG is a glycosaminoglycan residue of keratan sulfate excluding a reducing terminal galactose moiety, and (4) GAG is located at the 3-position, $R^3$ is located at the 4-position, $R^2$ is a $CH_2OSO_3H$ group and $R^3$ is an OH group when GAG is a glycosaminoglycan residue of keratan polysulfate excluding a reducing terminal galactose moiety.

A phospholipid- or lipid-linked glycosaminoglycan represented by the following formula or a salt thereof:

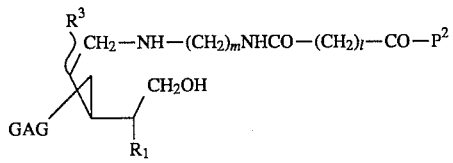
(VI)

wherein GAG, $R^1$ and $R^3$ are as defined in the foregoing formula (II), and m, l and $p^2$ are as defined in the foregoing formula (V).

A phospholipid- or lipid-linked glycosaminoglycan represented by the following formula or a salt thereof:

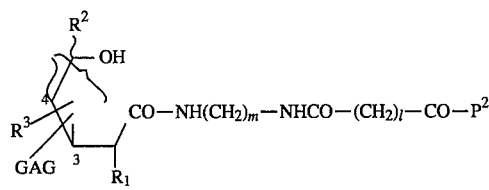
(VII)

wherein GAG, $R^1$, $R^2$ and $R^3$ are as defined in the foregoing formula (IV), and m, l and $p^2$ are as defined in the foregoing formula (V).

A phospholipid-linked glycosaminoglycan represented by the following formula or a salt thereof:

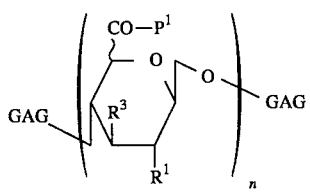
(VIII)

wherein $p^1$ is a phospholipid having a primary amino group and n is an integer not more than the number of carboxyl groups contained in glycosaminoglycan, and;

(1) each of $R^1$ and $R^3$ is an OH group when GAG is a glycosaminoglycan chain of hyaluronic acid, chondroitin, chondroitin sulfate A, C or E, or dermatan sulfate, (2) $R^1$ is an $OSO_3H$ group and $R^3$ is an OH group when GAG is a glycosaminoglycan chain of chondroitin sulfate D, (2) $R^1$ is an OH group and $R^3$ is an $OSO_3H$ group when GAG is a glycosaminoglycan chain of chondroitin sulfate K, (4) at least one of $R^1$ and $R^3$ is an $OSO_3H$ group while the other one is an OH group when GAG is a glycosaminoglycan chain of chondroitin polysulfate, and (5) $R^1$ is an OH group or an $OSO_3H$ group and $R_3$ is an OH group when GAG is a glycosaminoglycan chain of heparin or heparan sulfate.

Preferred molecular weights of the glycosaminoglycans are listed in Table 1.

The phospholipid having a primary amino group represented by $p^1$ in the foregoing formulae (I), (II), (III), (IV) and (VIII) is a compound represented by the formula:

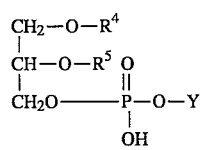
(IX)

wherein each of $R^4$ and $R^5$ is hydrogen, $—CH=CHR^6$ or $—COR^7$ (each of $R^6$ and $R^7$ is a $C_{6-24}$ alkyl group) and Y is $—CH_2CH_2NH—$ or

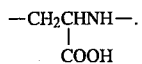

Particularly preferred are compounds in which either of $R^4$ and $R^5$ is a $—COR^7$ group such as hexadecanoyl or octadecanoyl or in which $R^4$ is a —CH=CHR$^6$ group and $R^5$ is a —COR$^7$ group.

The phospholipid or lipid represented by p$^2$ in the foregoing formulae (V), (VI) and (VII) is a compound represented by the formula:

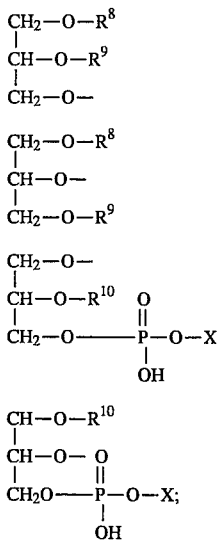

and wherein $R^8$ is hydrogen, $R^9$ is an alkyl group, $R^{10}$ is —CH=CHR$^6$ or —COR$^7$, wherein $R^6$ and $R^7$ are the same as above and X is —CH$_2$CH$_2$N$^+$(CH$_3$)$_3$ or an inositol residue. Particularly preferred are a lipid represented by the formula (X) or (XI) in which either of $R^8$ and $R^9$ is a —COR$^7$ group such as hexadecanoyl or octadecanoyl or in which $R^8$ is hydrogen and $R^9$ is a —COR$^7$ group, or a phospholipid represented by the formula (XII) or (XIII) in which $R^{10}$ is a —COR$^7$ group.

According to the present invention, the aforementioned phospholipid- or lipid-linked glycosaminoglycans are produced by the processes as listed below.

A process for producing a phospholipid-linked glycosaminoglycan represented by the foregoing formula (I) or a salt thereof which comprises the steps of;

reducing and cleaving the reducing terminal group of a glycosaminoglycan represented by the formula (I-1)

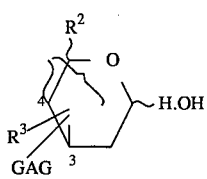

thereby obtaining a reduced product represented by the formula (I-2)

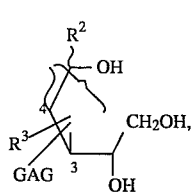

oxidizing the reduced product to obtain an oxidized product of the formula (I-3)

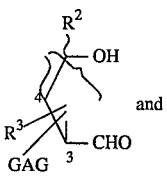

allowing an aldehyde group in the oxidized product to react with a primary amino group of a phospholipid, wherein GAG, $R^2$ and $R^3$ in the formulae (I-1), (I-2) and (I-3), are as defined in the formula (I).

A process for producing a phospholipid-linked glycosaminoglycan represented by the formula (II) or a salt thereof which comprises the steps of;

reducing and cleaving the reducing terminal group of a glycosaminoglycan represented by the formula (II-1)

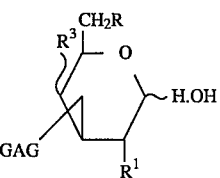

thereby obtaining a reduced product represented by the formula (II-2)

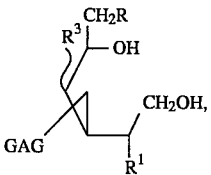

oxidizing the reduced product to obtain an oxidized product of the formula (II-3)

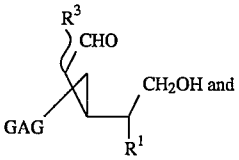

allowing an aldehyde group in the oxidized product to react with a primary amino group of a phospholipid, wherein GAG, $R^1$ and $R^3$ in the formulae (II-1), (II-2) and (II-3), are as defined in the foregoing formula (II) and R is an OH or OSO$_3$H group.

A process for producing a phospholipid-linked glycosaminoglycan represented by the formula (III) or a salt thereof which comprises the steps of;

oxidizing the reduced product represented by the formula (II-2) to obtain an oxidized product of the formula (11)

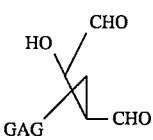

wherein GAG is as defined in the formula (III), and allowing an aldehyde group in the oxidized product to react with a primary amino group of a phospholipid.

A process for producing a phospholipid-linked glycosaminoglycan represented by the formula (IV) or a salt thereof which comprises the steps of;

oxidizing and cleaving the reducing terminal group of a glycosaminoglycan represented by the formula (12)

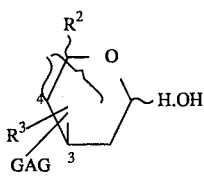

(12)

thereby obtaining an oxidized product represented by the formula (13)

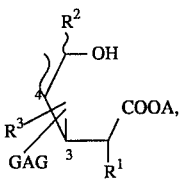

(13)

lactonizing the oxidized product to obtain a lactone represented by the formula (14)

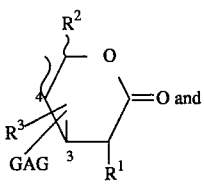

(14)

allowing the thus-obtained lactone to react with a primary amino group of a phospholipid, wherein GAG, $R^1$, $R^2$ and $R^3$ in the formulae (12), (13) and (14), are as defined in the formula (IV) and A is an alkali metal.

A process for producing a phospholipid- or lipid-linked glycosaminoglycan represented by the formula (V) or a salt thereof which comprises the steps of;

allowing an aldehyde compound represented by the formula (I-3) to react with an alkylene diamine to obtain a derivative represented by the formula (15)

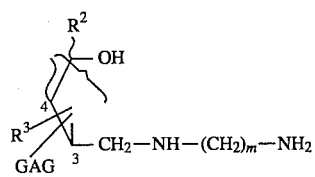

(15)

wherein GAG, $R^2$, $R^3$ and m are as defined in the formula (V), separately allowing a phospholipid or a lipid to react with a dicarboxylic acid or a dicarboxylic acid anhydride to obtain a phospholipid or lipid derivative having a carboxyl group, and allowing a primary amino group in the derivative of the formula (15) to react with the carboxyl group in the phospholipid or lipid derivative.

A process for producing a phospholipid- or lipid-linked glycosaminoglycan represented by the formula (VI) or a salt thereof which comprises the steps of;

allowing an aldehyde compound represented by the formula (II-3) to react with an alkylene diamine to obtain a derivative represented by the formula (16)

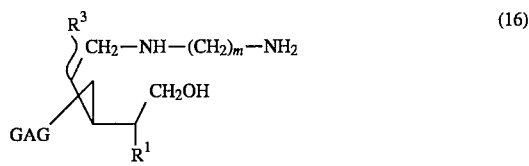

(16)

wherein GAG, $R^1$, $R^3$ and m are as defined in the formula (VI), separately allowing a phospholipid or a lipid to react with a dicarboxylic acid or a dicarboxylic acid anhydride to obtain a phospholipid or lipid derivative having a carboxyl group, and allowing a primary amino group in the derivative of the formula (16) to react with the carboxyl group in the phospholipid or lipid derivative.

A process for producing a phospholipid- or lipid-linked glycosaminoglycan represented by the formula (VII) or a salt thereof which comprises the steps of;

allowing a lactone compound represented by the formula (14) to react with an alkylene diamine to obtain a derivative represented by the formula (17)

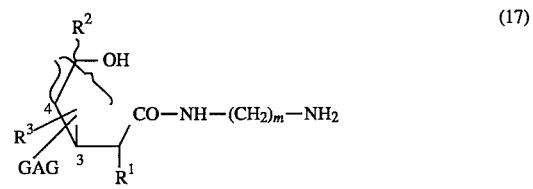

(17)

wherein GAG, $R^1$, $R^2$, $R^3$ and m are as defined in the formula (VII), separately allowing a phospholipid or a lipid to react with a dicarboxylic acid or a dicarboxylic acid anhydride to obtain a phospholipid or lipid derivative having a carboxyl group, and allowing a primary amino group in the derivative of the formula (17) to react with the carboxyl group in the phospholipid or lipid derivative.

A process for producing a phospholipid-linked glycosaminoglycan represented by the formula (VIII) or a salt thereof which comprises allowing a primary amino group of a phospholipid to react with, in the presence of a condensing agent, a carboxyl group of a glycosaminoglycan represented by the formula (18)

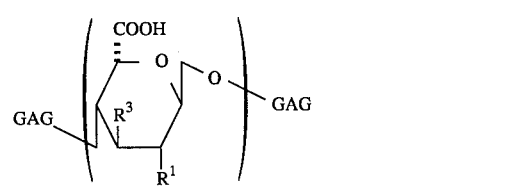

(18)

wherein GAG, $R^1$, $R^3$ and n are as defined in formula (VIII).

A process for producing a phospholipid-linked glycosaminoglycan represented by the formula (VIII) or a salt thereof which comprises the steps of; activating a carboxyl group of a glycosaminoglycan represented by the formula (18), and allowing the activated carboxyl group to react with a primary amino group of a phospholipid.

The processes for producing phospholipid- or lipid-linked glycosaminoglycans of the present invention are described in detail below.

Limited oxidation of reducing terminal group

In this process, the reducing terminal uronic acid, galactose or hexosamine moiety of a glycosaminoglycan is partially oxidized and cleaved to form an aldehyde group and the thus-formed aldehyde group is subjected to reductive alkylation reaction with a primary amino group of a phospholipid to give a phospholipid-linked glycosaminoglycan. The reaction scheme of this process is described below.

(A) In the case where glucuronic or iduronic acid in the reducing terminal sugar is subjected to the reaction:

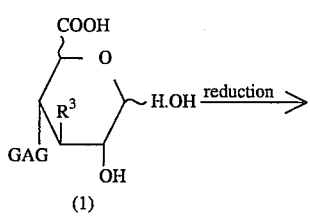
(1)

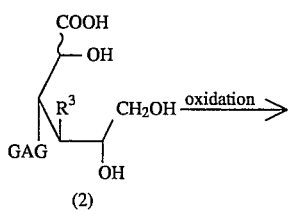
(2)

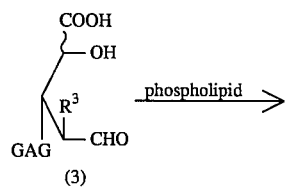
(3)

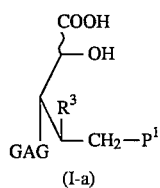
(I-a)

wherein $R^3$ is as defined above and $p^1$ is a phospholipid having a primary amino group.

In the case of using, as the starting material, hyaluronic acid, chondroitin, chondroitin sulfate A, chondroitin sulfate C, chondroitin sulfate E, chondroitin sulfate K, chondroitin polysulfate, dermatan sulfate and heparin, represented by the formula (1) having the reducing terminal D-glucuronic acid or L-iduronic acid in which an OH group is linked to the 2-position carbon atom, a phospholipid-linked glycosaminoglycan represented by the formula (I-a) is produced in accordance with the above reaction scheme.

(B) In the case where glucosamine or galactosamine in the reducing terminal sugar is subjected to the reaction:

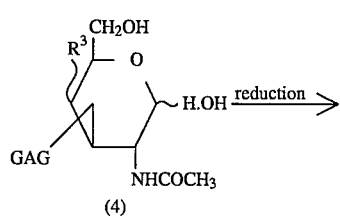
(4)

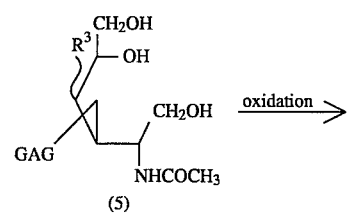
(5)

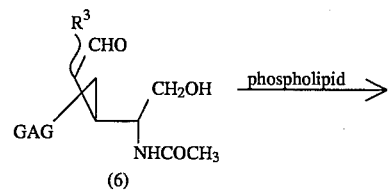
(6)

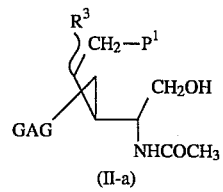
(II-a)

wherein $R^3$ is as defined above and $p^1$ is a phospholipid having a primary amino group.

In the case of using, as the starting material, hyaluronic acid, chondroitin, chondroitin sulfate A, chondroitin sulfate K, chondroitin polysulfate and dermatan sulfate, represented by the formula (4) having glucosamine or galactosamine as the reducing terminal group in which a $CH_2OH$ group is linked to the 5-position carbon atom, a phospholipid-linked glycosaminoglycan represented by the formula (II-a) is produced in accordance with the above reaction scheme.

(C) In the case where galactose in the reducing terminal sugar is subjected to the reaction:

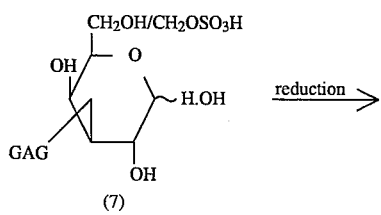
(7)

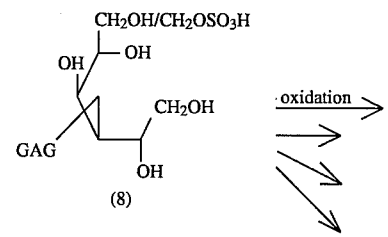
(8)

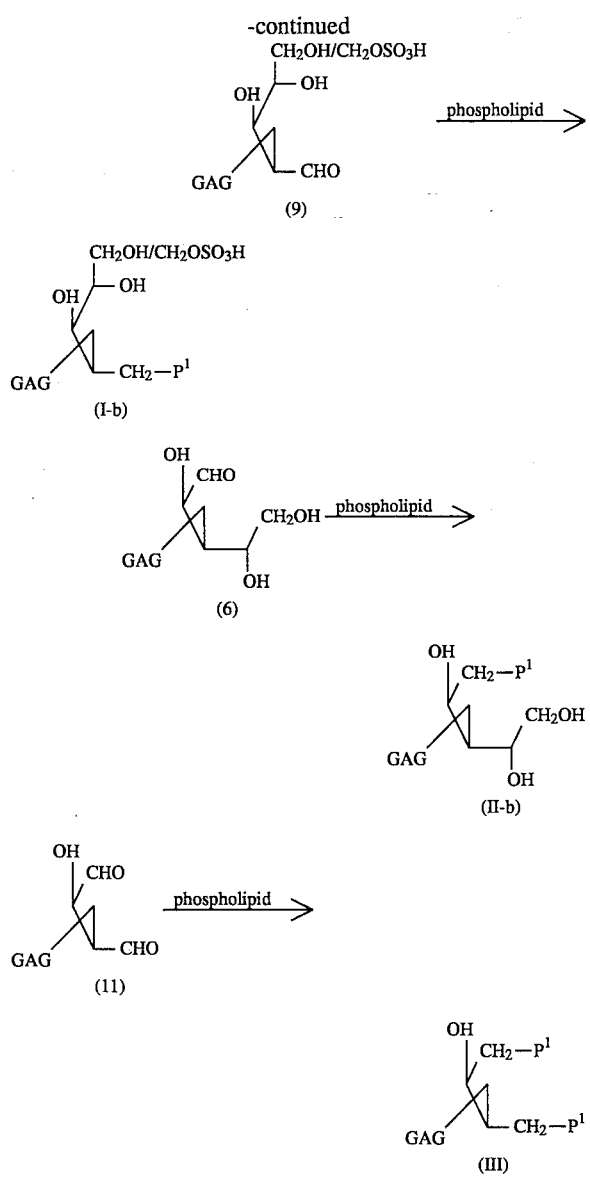

preferably from 25 to 30 equivalents, per mole of compound (1), (4) or (7).

The thus obtained compounds of the formulae (2), (5) and (8) are then subjected to partial oxidation to form aldehyde compounds represented by formulae (3), (6), (9), (10) and (11).

Usable as an oxidation agent in the oxidation reaction is an alkali salt of periodic acid such as sodium periodate, potassium periodate or the like.

The amount of the oxidation agent ranges from 1 to 10 equivalents, preferably from 3 to 6 equivalents, per mole of the compound (2), (5) or (8). The oxidation reaction may be effected at a temperature of from 0° to 10° C., preferably from 0° to 4° C.

Each of the thus-formed aldehyde compounds (3), (6), (9), (10) and (11) can be reacted with a primary amino group of a phospholipid in accordance with the known reductive alkylation. Thus, the phospholipid-linked glycosaminoglycans of the present invention represented by the formulae (I-a), (II-a), (I-b), (II-b) and (III) are obtained.

Examples of phospholipids to be used in the above reaction include L-(α-phosphatidyl)ethanolamine, DL-phosphatidyl-L-serine, ethanolamine plasmalogen, serine plasmalogen and the like.

The reductive alkylation reaction for the production of the compounds represented by the formulae (I-a), (II-a), (I-b), (II-b) and (III) may be effected by mixing the aldehyde compound (3), (6), (9), (10) or (11) and a phospholipid dissolved in chloroform or the like uniformly in a solvent such as water, 0.05M phosphate buffer (pH 7.0) or dimethylformamide and allowing the mixture to react at a temperature of from 15° to 60° C., and simultaneously or thereafter carrying out a reduction reaction using a reducing agent such as sodium cyanoboron hydride or the like.

Examples of compounds which are produced by the limited reducing terminal group oxidation are shown in Table A.

wherein $R^3$ is as defined above and $p^1$ is a phospholipid having a primary amino group.

In the case of using keratan sulfate and keratan polysulfate represented by the above formula (7) as the starting material having galactose as the reducing terminal sugar, a phospholipid-linked glycosaminoglycan represented by the formula (I-b), (II-b) or (III) is produced in accordance with the above reaction scheme.

In the above processes (A), (B) and (C), the reducing terminal sugar moieties of glycosaminoglycans represented by the formulae (1), (4) and (7) are first subjected to reduction cleavage to obtain corresponding compounds (2), (5) and (8).

Usable as a reducing agent in the reduction step is an alkali salt of boron hydride such as sodium boron hydride, sodium cyanoboron hydride or the like.

As a solvent for use in the above reduction reaction, water or a 0.05% borate buffer (pH 8.3) may be used.

The reduction reaction may be effected at a temperature of from 10° to 30° C., preferably from 15° to 25° C.

The amount of the reducing agent, though varying depending on its type, ranges from 5 to 50 equivalents,

TABLE A

| Compound No. | Formula | Glycosaminoglycan material |
|---|---|---|
| I-(1) | COOH, OH, OH, GAG, CH₂—P¹ | hyaluronic acid, chondroitin, chondroitin sulfate A, C or E, dermatan sulfate, heparin, heaparan sulfate |
| I-(2) | COOH, OH, OSO₃H, GAG, CH₂—P¹ | chondroitin sulfate K, chondroitin polysulfate |
| I-(3) | CH₂OH, HO, OH, GAG, CH₂—P¹ | keratin sulfate |
| I-(4) | CH₂OSO₃H, HO, OH, GAG, CH₂—P¹ | keratin polysulfate |

TABLE A-continued

| Compound No. | Formula | Glycosaminoglycan material |
|---|---|---|
| II-(1) | ![structure with HO, CH₂—P¹, CH₂OH, GAG, NHCOCH₃] | hyaluronic acid, chondroitin |
| II-(2) | ![structure with HO₃SO, CH₂—P¹, CH₂OH, GAG, NHCOCH₃] | chondroitin sulfate A or K, chondroitin polysulfate, dermatan sulfate |
| II-(3) | ![structure with HO, CH₂—P¹, CH₂OH, GAG, OH] | keratan sulfate, keratan polysulfate |
| III | ![structure with HO, CH₂—P¹, GAG, CH₂—P¹] | keratan sulfate, keratin polysulfate |

Lactonization of reducing terminal group

In this process, the reducing terminal uronic acid, galactose or hexosamine moiety of a glycosaminoglycan is subjected to oxidation to cleave the reducing terminal sugar moiety and the cleaved product is lactonized and reacted with a primary amino group of a phospholipid to obtain a phospholipid-linked glycosaminoglycan. This reaction scheme is illustrated below.

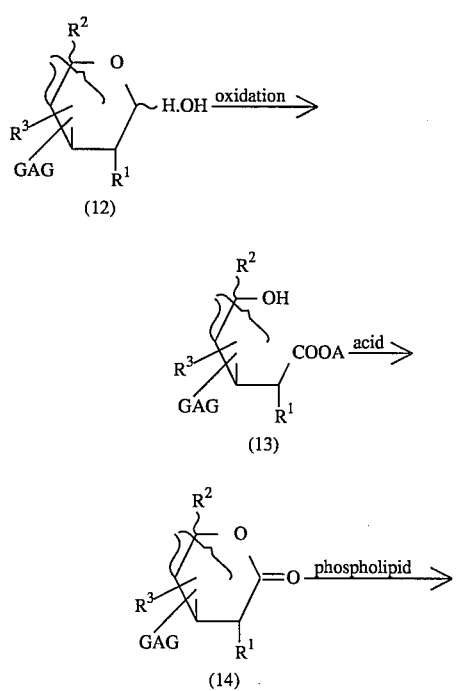

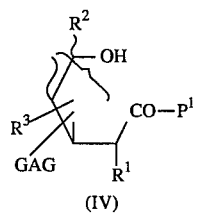

(IV)

wherein each of $R^1$, $R^2$ and $R^3$ is as defined above, $p^1$ is a phospholipid having a primary amino group and A is an alkali metal.

According to this process, a glycosaminoglycan represented by the formula (12) is firstly subjected to oxidation to cleave its reducing terminal moiety, thereby obtaining a carboxyl compound represented by formula (13).

Usable as a starting material are compounds represented by the above formula (12) including hyaluronic acid, chondroitin, chondroitin sulfate A, chondroitin sulfate C, chondroitin sulfate D, chondroitin sulfate E, chondroitin sulfate K, chondroitin polysulfate, dermatan sulfate, heparin, heparan sulfate, keratan sulfate and keratan polysulfate.

Iodine, bromine or the like may be used in the oxidizing step as the oxidation agent.

The amount of the oxidation agent ranges from 2 to 20 equivalents, preferably from 5 to 15 equivalents, per mole of the compound of formula (12).

Water or a 0.05M phosphate buffer (pH 7.0) may be used as the solvent in the oxidation reaction.

The oxidation reaction may be effected at a temperature of from 0° to 40° C., preferably from 15° to 20° C.

The thus obtained compound of the formula (13) is then subjected to acid treatment to form a lactone compound represented by formula (14).

A strongly acidic cation exchange resin such as Dowex 50, Amberlite IR 120 or the like may be used in the acid treatment.

The thus-formed lactone compound of formula (14) is then allowed to react with a phospholipid to produce a phospholipid-linked glycosaminoglycan of the present invention represented by formula (IV).

The same phospholipid compounds as described in the foregoing limited reducing terminal group oxidation process may be used in this reaction step.

The reaction of the lactone compound of formula (14) with a phospholipid for the production of the compound represented by formulae (IV) may be effected by dissolving the lactone compound of formula (14) in a solvent such as water, 0.05M phosphate buffer (pH 7.0) or dimethylformamide, and mixing the solution with a phospholipid dissolved in chloroform or the like uniformly and allowing the mixture to react at a temperature of from 5° to 80° C., preferably from 30° to 60° C.

Examples of compounds which are produced by the reducing terminal group lactonization process are shown in Table B.

TABLE B

| Compound No. | Formula | Glycosaminoglycan material |
|---|---|---|
| IV-(1) | GAG–[COOH, OH, OH, CO–P¹, OH] | hyaluronic acid, chondroitin, chondroitin sulfate A, C or E, dermatan sulfate, heparin, heaparan sulfate |
| IV-(2) | GAG–[COOH, OH, OH, CO–P¹, OSO₃H] | chondroitin sulfate D, heparin, heparin sulfate |
| IV-(3) | GAG–[COOH, OH, OSO₃H, CO–P¹, OH] | chondroitin sulfate K |
| IV-(4)-a | GAG–[COOH, OH, OSO₃H, CO–P¹, OSO₃H] | chondroitin polysulfate |
| IV-(4)-b | GAG–[COOH, OH, OSO₃H, CO–P¹, OH] | chondroitin polysulfate |
| IV-(4)-c | GAG–[COOH, OH, OH, CO–P¹, OSO₃H] | chondroitin polysulfate |
| IV-(5) | GAG–[CH₂OH, HO, OH, CO–P¹, OH] | keratan sulfate |
| IV-(6) | GAG–[CH₂OSO₃H, HO, OH, CO–P¹, OH] | keratan polysulfate |

TABLE B-continued

| Compound No. | Formula | Glycosaminoglycan material |
|---|---|---|
| IV-(7) | GAG, HO, CH$_2$OH, OH, CO—P$^1$, NHCOCH$_3$ | hyaluronic acid, chondroitin |
| IV-(8) | GAG, HO$_3$SO, CH$_2$OH, OH, CO—P$^1$, NHCOCH$_3$ | chondroitin sulfate A or K, dermantan sulfate |
| IV-(9) | GAG, HO, CH$_2$OSO$_3$H, OH, CO—P$^1$, NHCOCH$_3$ | chondroitin sulfate C or D |
| IV-(10) | GAG, HO$_3$SO, CH$_2$OSO$_3$H, OH, CO—P$^1$, NHCOCH$_3$ | chondroitin sulfate E |
| IV-(11)-a | GAG, HO$_3$SO, CH$_2$OH, OH, CO—P$^1$, NHCOCH$_3$ | chondroitin polysulfate |
| IV-(11)-b | GAG, HO, CH$_2$OSO$_3$H, OH, CO—P$^1$, NHCOCH$_3$ | chondroitin polysulfate |
| IV-(11)-c | GAG, HO$_3$SO, CH$_2$OSO$_3$H, OH, CO—P$^1$, NHCOCH$_3$ | chondroitin polysulfate |
| IV-(12) | GAG, CH$_2$OSO$_3$H, OH, OH, CO—P$^1$, NHSO$_3$H | heparin |

TABLE B-continued

| Compound No. | Formula | Glycosaminoglycan material |
|---|---|---|
| IV-(13)-a | GAG—[ring: CH₂OH, OH, OSO₃H, CO—P¹, NHCOCH₃/NHSO₃H] | heparan sulfate |
| IV-(13)-b | GAG—[ring: CH₂OSO₃H, OH, OH, CO—P¹, NHCOCH₃/NHSO₃H] | heparan sulfate |
| IV-(13)-c | GAG—[ring: CH₂OSO₃H, OH, OSO₃H, CO—P¹, NHCOCH₃/NHSO₃H] | heparan sulfate |
| IV-(14) | GAG—[ring: CH₂OSO₃H, OH, OH, CO—P¹, NHCOCH₃] | keratan sulfate, keratan polysulfate |

Amidation of reducing terminal group

In this process, each of the aldehyde compounds represented by the formulae (3), (6), (9) and (10) and the lactone compound represented by formula (14) is allowed to react with an alkylenediamine compound to obtain a glycosaminoglycan derivative having a primary amino group in its reducing terminal group. The thus-obtained glycosaminoglycan derivative having a primary amino group is then allowed to react with a phospholipid or lipid derivative having carboxyl group such that the primary amino group and the carboxyl group are linked together. Thus, a phospholipid- or lipid-linked glycosaminoglycan is produced. The reaction scheme of this process is illustrated below.

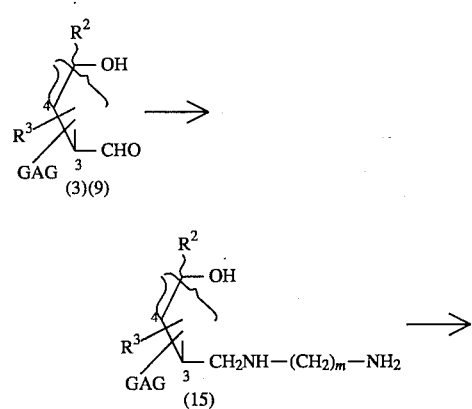

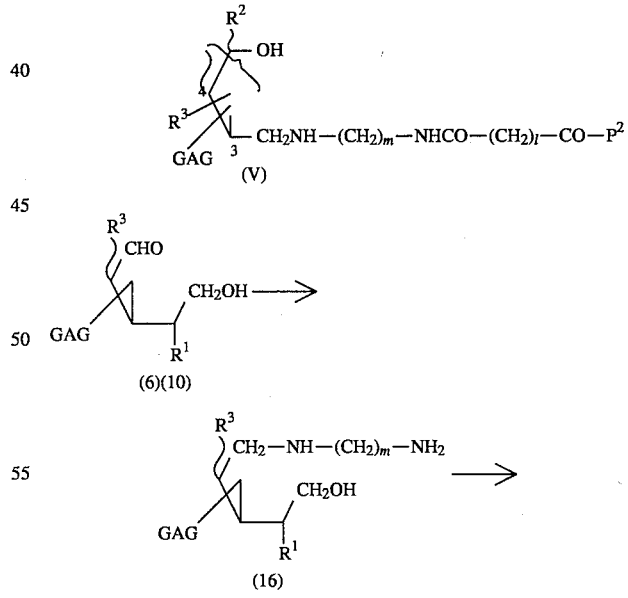

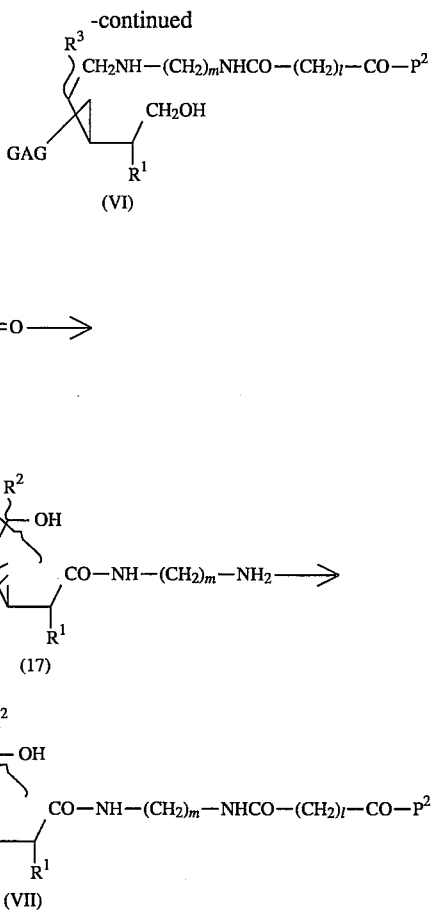

wherein each of $R^1$, $R^2$ and $R^3$ is as defined above and $p^2$ is a phospholipid or a lipid.

A glycosaminoglycan derivative having a primary amino group in its reduction terminus, as represented by the above formula (15), (16) or (17), is obtained by allowing each of compounds (3), (6), (9) and (10) prepared by the aforementioned limited reducing terminal oxidation process, and compound (14) prepared by the aforementioned reducing terminal lactonization process to react with an alkylenediamine compound in the presence of a reducing agent.

An alkylenediamine compound usable in this reaction may be selected from compounds represented by the formula

wherein m is an integer of from 1 to 8.

Sodium cyanoboron hydride or the like may be used as the reducing agent.

The amount of the reducing agent ranges from 10 to 100 moles per mole of the glycosaminoglycan to be used in the reaction system.

Water or a 0.05M phosphate buffer may be used as the reaction solvent.

The reaction may be effected at a temperature of from 0° to 60° C., preferably from 4° to 25° C.

A phospholipid or lipid derivative having a carboxyl group may be obtained by allowing a phospholipid or lipid compound having a hydroxyl group in its glycerol structure to react with a dicarboxylic acid or a dicarboxylic acid anhydride.

Examples of the phospholipid or lipid compound to be used in this reaction include monoacylglycerol, diacylglycerol, lysophosphatidylcholine, lysophosphatidylinositol, ether lipids, ether phospholipids and the like.

Succinic acid, glutaric acid, adipic acid or the like may be used as the dicarboxylic acid.

Maleic anhydride, succinic anhydride, fumaric anhydride or the like may be used as the dicarboxylic acid anhydride.

1-ethyl-3-(di-methylaminopropyl)carbodiimide, dicyclohexylcarbodiimide or the like may be used as the condensing agent.

Chloroform, acetanilide, dimethylformamide or the like may be used as the reaction solvent.

The reaction temperature may range from 0° to 60° C. when a dicarboxylic acid is used in the presence of a condensing agent, or from 20° to 80° C. when a dicarboxylic acid anhydride is used.

The reaction of a glycosaminoglycan derivative having a primary amino group in its reducing terminal group with a phospholipid or lipid derivative having a carboxyl group may be effected by first activating the carboxyl group in the phospholipid or lipid derivative in accordance with the well known means in the field of peptide chemistry, and then allowing the resulting activated compound to react with the glycosaminoglycan derivative.

Activation of the carboxyl group in the phospholipid or lipid derivative may be effected by converting the carboxyl group into an active ester through reaction of the phospholipid or lipid derivative with N-hydroxysuccinimide, p-nitrophenol, N-hydroxybenzotriazole, N-hydroxypiperidine, N-hydroxysuccinamide, 2,4,5-tri-chlorophenol or the like in the presence of a condensing agent.

Chloroform, acetonitrile, dimethylformamide or the like or a mixture thereof may be used as the reaction solvent. 1-ethyl-3-(dimethylaminopropyl)carbodiimide, dicyclohexylcarbodiimide or the like may be used as the condensing agent.

The reaction may be effected at a temperature of from 0° to 60° C.

The thus-obtained phospholipid or lipid derivative in which the carboxyl group has been activated is then allowed to react with the glycosaminoglycan derivative of formulae (15), (16) or (17) having a primary amino group to obtain the phospholipid or lipid-linked glycosaminoglycans of formulae (V), (VI) and (VII). The solvent used in this reaction is chloroform, acetonitrile, dimethylformamide or a mixture thereof. The reaction temperature ranges from 0° to 60° C.

Illustrative examples of compounds which are produced by the above reducing terminal group amination process are shown in Table C.

TABLE C

| Compound No. | Formula | Glycosaminoglycan material |
|---|---|---|
| V-(1) | GAG—[ring with COOH, OH, OH, CH$_2$—R] | hyaluronic acid, chondroitin, chondroitin sulfate A, C or E, dermatan sulfate, heparin, heaparan sulfate |
| V-(2) | GAG—[ring with COOH, OH, OSO$_3$H, CH$_2$—R] | chondroitin sulfate K, chondroitin polysulfate |
| V-(3) | GAG—[ring with CH$_2$OH, OH, HO, CH$_2$—R] | keratin sulfate |
| V-(4) | GAG—[ring with CH$_2$OSO$_3$H, OH, HO, CH$_2$—R] | keratin polysulfate |
| VI-(1) | GAG—[ring with CH$_2$—R, HO, CH$_2$OH, NHCOCH$_3$] | hyaluronic acid, chondroitin |
| VI-(2) | GAG—[ring with CH$_2$—R, HO$_3$SO, CH$_2$OH, NHCOCH$_3$] | chondroitin sulfate A or K, chondroitin polysulfate, dermantan sulfate |
| VI-(3) | GAG—[ring with CH$_2$—R, HO, CH$_2$OH, OH] | keratan sulfate, keratan polysulfate |
| VII-(1) | GAG—[ring with COOH, OH, OH, CO—R, OH] | hyaluronic acid, chondroitin, chondroitin sulfate A, C or E, dermatan sulfate, heparin, heaparan sulfate |
| VII-(2) | GAG—[ring with COOH, OH, OH, CO—R, OSO$_3$H] | chondroitin sulfate D, heparin, heparin sulfate |

TABLE C-continued

| Compound No. | Formula | Glycosaminoglycan material |
|---|---|---|
| VII-(3) | GAG–CH(OSO$_3$H)–CH(COOH)(OH) ... CO—R, OH | chondroitin sulfate K |
| VII-(4)-a | GAG–CH(OSO$_3$H)–CH(COOH)(OH) ... CO—R, OSO$_3$H | chondroitin polysulfate |
| VII-(4)-b | GAG–CH(OSO$_3$H)–CH(COOH)(OH) ... CO—R, OH | chondroitin polysulfate |
| VII-(4)-c | GAG–CH(OH)–CH(COOH)(OH) ... CO—R, OSO$_3$H | chondroitin polysulfate |
| VII-(5) | GAG–C(HO)(CH$_2$OH)(OH) ... CO—R, OH | keratan sulfate |
| VII-(6) | GAG–C(HO)(CH$_2$OSO$_3$H)(OH) ... CO—R, OH | keratan polysulfate |
| VII-(7) | GAG–C(HO)(CH$_2$OH)(OH) ... CO—R, NHCOCH$_3$ | hyaluronic acid, chondroitin |
| VII-(8) | GAG–C(HO$_3$SO)(CH$_2$OH)(OH) ... CO—R, NHCOCH$_3$ | chondroitin sulfate A or K, dermantan sulfate |

TABLE C-continued

| Compound No. | Formula | Glycosaminoglycan material |
|---|---|---|
| VII-(9) | CH$_2$OSO$_3$H, OH, HO, GAG, CO—R, NHCOCH$_3$ | chondroitin sulfate C or D |
| VII-(10) | CH$_2$OSO$_3$H, OH, HO$_3$SO, GAG, CO—R, NHCOCH$_3$ | chondroitin sulfate E |
| VII-(11)-a | CH$_2$OH, OH, HO$_3$SO, GAG, CO—R, NHCOCH$_3$ | chondroitin polysulfate |
| VII-(11)-b | CH$_2$OSO$_3$H, OH, HO, GAG, CO—R, NHCOCH$_3$ | chondroitin polysulfate |
| VII-(11)-c | CH$_2$OSO$_3$H, OH, HO$_3$SO, GAG, CO—R, NHCOCH$_3$ | chondroitin polysulfate |
| VII-(12) | CH$_2$OSO$_3$H, OH, OH, GAG, CO—R, NHSO$_3$H | heparin |
| VII-(13)-a | CH$_2$OH, OH, OSO$_3$H, GAG, CO—R, NHCOCH$_3$/NHSO$_3$H | heparan sulfate |
| VII-(13)-b | CH$_2$OSO$_3$H, OH, OH, GAG, CO—R, NHCOCH$_3$/NHSO$_3$H | heparan sulfate |

TABLE C-continued

| Compound No. | Formula | Glycosaminoglycan material |
|---|---|---|
| VII-(13)-c | 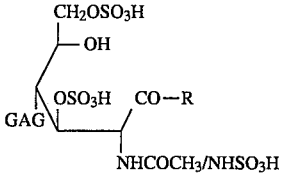 | heparan sulfate |
| VII-(14) | 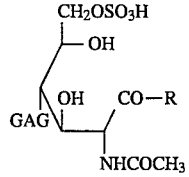 | keratan sulfate, keratan polysulfate |

Application of condensing agent

Each member of the glycosaminoglycans, excluding keratan sulfate and keratan polysulfate, contains D-glucuronic acid or L-iduronic acid as the uronic acid moiety, and each of these acids has a carboxyl group linked to its 5-position carbon atom.

In this process, a phospholipid-linked glycosaminoglycan is produced by allowing the uronic acid carboxyl group to react with a primary amino group of a phospholipid in the presence of a condensing agent.

The reaction scheme of this process is illustrated below.

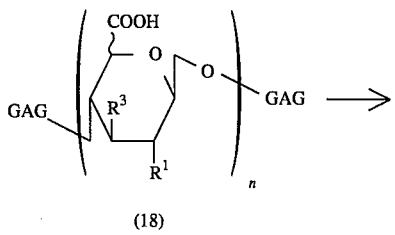

(18)

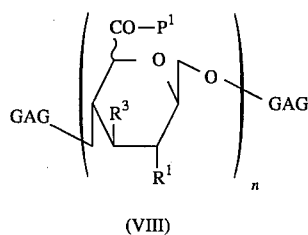

(VIII)

wherein each of $R^1$, $R^3$, n and $p^1$ is as defined above.

Compounds represented by the formula (18) to be used as the starting material are selected from hyaluronic acid, chondroitin, chondroitin sulfate A, chondroitin sulfate C, chondroitin sulfate D, chondroitin sulfate E, chondroitin sulfate K, chondroitin polysulfate, dermatan sulfate, heparin and heparan sulfate.

Any of the compounds described in the foregoing illustration of the limited reducing terminal group oxidation process may be used as the phospholipid.

Examples of the condensing agent include diethylcarbodiimide, diisopropylcarbodiimide, methylpropylcarbodiimide, dicyclohexylcarbodiimide, hexamethylenecarbodiimide, heptanemethylenecarbodiimide, 1-ethyl- 3-(3-dimethylaminopropyl)carbodiimide, 1-cyclohexyl-3-(2-morpholinoethyl)carbodiimide-meso-p-toluenesulfonate, 1-t-butyl-3-(3-dimethylaminopropyl) carbodiimide, diphenylcarbodiimide, 4,4'-dinitrodiphenylcarbodiimide, di-p-tolylcarbodiimide, bis-(trimethylsilyl)carbodiimide and the like.

The condensing agent may be used in an amount of from 10 to 100 moles per mole of a phospholipid or lipid to be used.

The reaction may be effected at a temperature of from 4° to 60° C., preferably from 15° to 25° C., in a solvent such as dimethylformamide, chloroform or a mixture thereof.

Illustrative examples of compounds which are produced by the condensation process are shown in Table D.

TABLE D

| Compound No. | Formula | Glycosaminoglycan material |
|---|---|---|
| VIII-(1) | | hyaluronic acid, chondroitin, chondroitin sulfate A, C or E, dermatan sulfate |
| VIII-(2) | | chondroitin sulfate D |
| VIII-(3) | | chondroitin sulfate K |
| VIII-(4)-a | | chondroitin polysulfate |
| VIII-(4)-b | | chondroitin polysulfate |
| VIII-(4)-c | | chondroitin polysulfate |

TABLE D-continued

| Compound No. | Formula | Glycosaminoglycan material |
|---|---|---|
| VIII-(5)-a | (structure with CO—P¹, OH, OH, O, O, GAG, GAG)$_n$ | heparin, heparan sulfate |
| VIII-(5)-b | (structure with CO—P¹, OH, OSO₃H, O, O, GAG, GAG)$_n$ | heparin, heparan sulfate |

Activation of glycosaminoglycan

In this process, similar to the case of the aforementioned condensing agent-applied process, the phospholipid-linked glycosaminoglycan (VIII) is produced by activating the uronic acid carboxyl group and then binding the activated carboxyl group to a primary amino group in a phospholipid.

The same glycosaminoglycan compounds and phospholipid compounds as described in the foregoing condensing agent-applied process may be used in this process.

Activation of the carboxyl group in the uronic acid moiety of a glycosaminoglycan compound may be effected by well known means in the field of peptide chemistry, for example by converting the carboxyl group into an active ester through reaction of the glycosaminoglycan compound with N-hydroxysuccinimide, p-nitrophenol, N-hydroxybenzotriazole, N-hydroxypiperidine, N-hydroxysuccinamide, 2,4,5-trichlorophenol or the like in the presence of a condensing agent.

The carboxyl group of the uronic acid moiety may be subjected to the reaction as a form of amine salt such as of tri(n-butyl)amine salt, triethylamine salt, pyridine salt or the like.

Dimethylformamide, pyridine, dimethylsulfoxide or the like may be used as the reaction solvent.

1-ethyl-3-(dimethylaminopropyl)carbodiimide, dicyclohexylcarbodiimide or the like may be used the condensing agent.

The reaction may be effected at a temperature of from 0° to 60° C., preferably from 4° to 20° C.

By allowing the thus obtained carboxyl group-activated glycosaminoglycan to react with a phospholipid, a phospholipid-linked glycosaminoglycan of formula (VIII) is obtained.

This reaction may be effected by allowing the activated glycosaminoglycan to react with a phospholipid at a temperature of from 0° to 90° C., preferably from 25° to 60° C. in a solvent such as dimethylformamide, chloroform or a mixture thereof.

The contents of phospholipid or lipid portions in the phospholipid- or lipid-linked glycosaminoglycans of the present invention represented by the formulae (I) to (VIII) may range from 0.005 to 50%, preferably from 2 to 10%.

Separation and purification of the phospholipid- or lipid-linked glycosaminoglycans obtained by the aforementioned processes may be carried out for instance in the following manner. The final reaction solution in each procedure is mixed with ethanol which has been saturated with sodium acetate and the resulting precipitate is filtered out to remove unreacted phospholipid or lipid. The thus-separated precipitates are subjected to hydrophobic chromatography and the carrier is washed with an aqueous solution of a salt such as ammonium acetate, ammonium chloride, sodium chloride or the like to remove unreacted glycosaminoglycan. Thereafter, the phospholipid- or lipid-linked glycosaminoglycan absorbed to the carrier is eluted with an aqueous solution of 10 to 50% methanol.

The metastasis inhibitor of the present invention may be prepared preferably by mixing each of the phospholipid- or lipid-linked glycosaminoglycans represented by formulae (I) to (VIII), or its pharmacologically acceptable salt, with solid or liquid carriers or diluents for medical use, that is, additive agents such as fillers, stabilizers and the like.

Since the salt form of the phospholipid- or lipid-linked glycosaminoglycan is soluble in water, it is suitable to formulate it into injectable solutions. The amount of the active ingredient in the medical preparation may be varied within the range of from 1 to 90% by weight based on the weight of the carrier.

The active compound may be orally administered in the form of granules, fine granules, powders, tablets, capsules, pills or solutions, as well as bulk powders, or administered by intravenous, intramuscular or subcutaneous injection. The active compound may also be used as external preparations such as suppositories, ointments, cataplasmas, plasters, liniments, lotions and the like. Also, it may be made into powder for injection use which is dissolved in an appropriate liquid upon use.

For the preparation of pharmaceuticals containing the phospholipid- or lipid-linked glycosaminoglycans of the present invention or their salts, any organic or inorganic, and solid or liquid carrier or diluent may be used provided that such additives are acceptable for oral, intestinal, parenteral or topical administration. Carriers to be used in the present invention include water, gelatin, lactose, starch, magnesium stearate, talc, animal and plant oils, benzyl alcohol, gum, polyalkylene glycol, petroleum resins, coconut oil, lanolin and other carriers for medical use. In addition, levels of stabilizers, moistening agents, emulsifying agents, as well as salts for adjusting osmotic pressure or maintaining appropriate pH value of the pharmaceutical preparations.

In the case of granules, fine granules, powders, tablets or capsules, the pharmaceutical preparation may contain the active ingredient of the present invention preferably in an amount of from 5 to 80% by weight, while 1 to 30% by weight may be preferable in the case of solutions. Further, preferred contents of the active ingredient may be in the range of from 1 to 10% by weight in the case of injections, from 1 to 50% by weight in the case of suppositories, and from 0.1 to 10% by weight in the case of ointments, cataplasmas and the like for use in topical administration.

Clinical dose may preferably be in the range of from 100 to 2,000 mg in terms of the amount of the active ingredient per day per adult in the case of oral administration, though the dose may be varied depending on ages and symptoms. Preferably, the above daily dose may be administered once a day or two or three times a day by dividing the dose accordingly.

When used as injections, preferred dose may be in the range of from 100 to 1,000 mg in terms of the amount of the active ingredient per day per adult. When used as ointments, cataplasmas and the like, these preparations with the aforementioned contents of the active ingredient may be applied to an affected part in an appropriate amount.

With regard to acute toxicity of the active ingredient, animal tests were carried out in the following manner. Four-week-old male and female Sic-ddy mice were preliminarily fed for one week and, when the males grew to weigh 23 to 30 g and the females to weigh 20 to 25 g, HA1-PPEADP (lot No. 300) and CS(S3)-PPEADP (lot No. 302-2; both PPEADPs are described later) were dissolved in a physiological saline ordained by The Pharmacopoea of Japan to a concentration of 5% and intraperitoneally administered to the mice. The intraperitoneal administration was applied to this test because of its most frequent generation of the toxicity symptoms. 10 males and 10 females were used in each test group. As a result, it was found that the $LD_{50}$ value in each test plot was 2,000 mg/kg or higher, thus proving the safety of the compound of the present invention as a drug.

BEST MODE TO PRACTICE THE INVENTION

Figure 1:
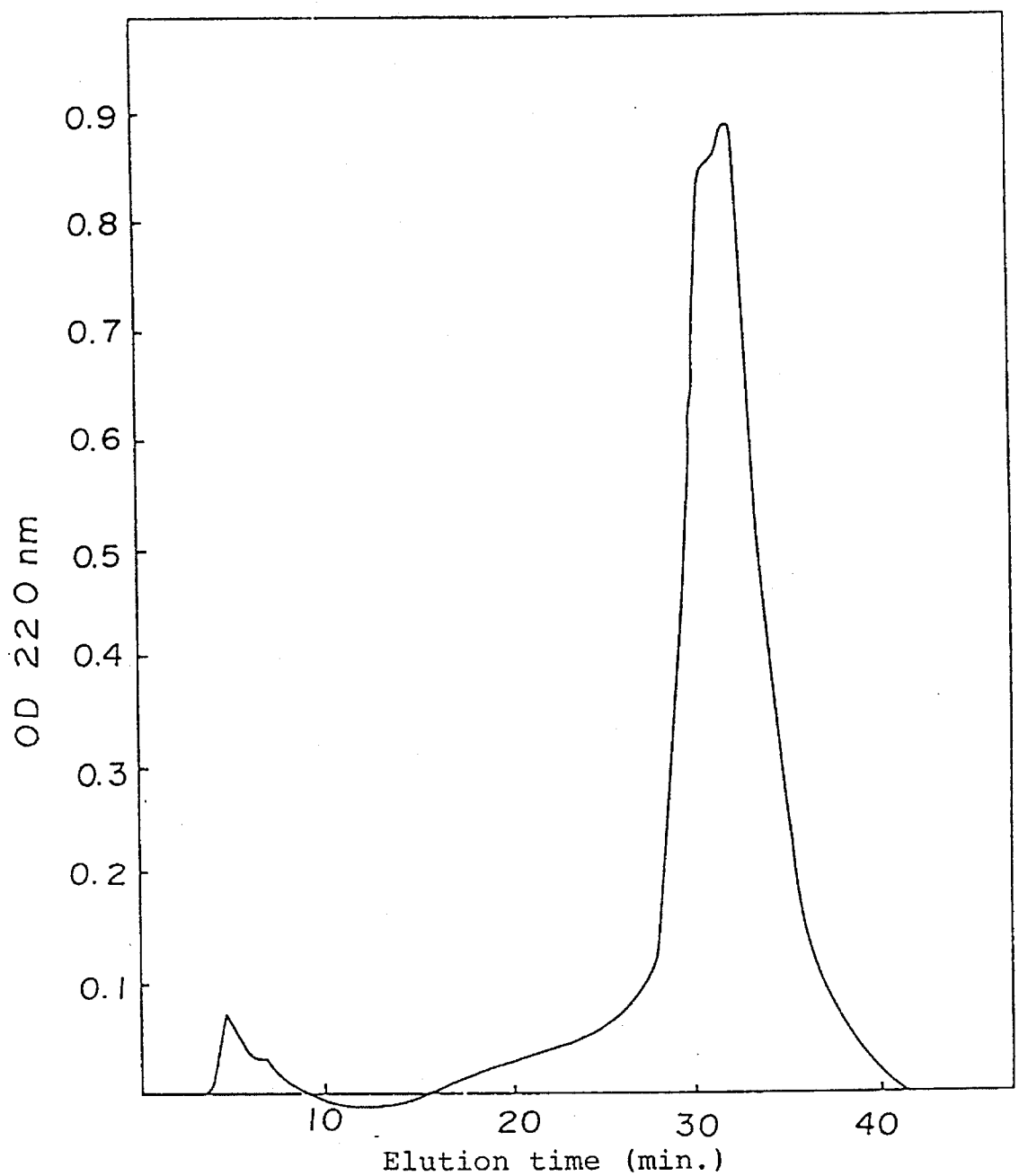
FIGS. 1 to 6 show data on the hydrophobic chromatography of phospholipid- or lipid-linked glycosaminoglycans produced in Example 1-(2)-1), Example 2-(2)-1), Example 2-(3), Example 4-(1), Example 5-(1) and Example 5-(2), respectively.

The present invention is described in detail below with reference to the following Examples which are not construed to limit the scope of the present invention.

In the following examples, contents of phosphorus, phospholipid or lipid and glycosaminoglycan (GAG) in phospholipid- or lipid-linked gylcosaminoglycan were measured in the following manner.

Measuring Method
1. Determination of GAG
  (1) GAG containing uronic acid: Carbazole sulfuric acid method (Bitter-Muir method) (*Analytical Biochemistry*, 4, 330–334, 1962).
  (2) Keratan sulfate or keratan polysulfate containing galactose: Anthrone method (*Biochem. J.*, 50, 298–303, 1952).
2. Determination of phospholipid or lipid
  (1) Phosphorus: Molybdenum blue method (*Inorganic Applied Colorimetric Analysis*, vol. 4, pp. 130–135 (representative editor, Shiro Hirano; published by Kyoritsu Shuppan).
  (2) Fatty acid: A 10 to 50 mg portion of GAG-lipid is dissolved in 10 ml of 1N sodium hydroxide solution and hydrolyzed at 100° C. for 1 hour. The resulting reaction mixture is adjusted to an acidic pH with 1N hydrochloric acid solution and extracted with chloroform, and the chloroform phase is washed with water. After drying with dehydrated Glauber's salt, the solvent is removed under a reduced pressure. The resulting residue is sealed in a tube together with an appropriate volume of methanol containing 3% HCl (gas), heated at 100° C. for 3 hours and then extracted three times with petroleum ether. The resulting petroleum ether phase is washed three times with water to remove contaminated hydrochloric acid. After drying with Glauber's salt, the resulting product is concentrated under a reduced pressure and subjected to the following gas-liquid chromatography.

Gas-liquid chromatography (GLC)
GC-15A (Shimadzu Corp.)
Loading material: PEG-HT 5% Uniport HP 60/80 (Gasukuro Kogyo Inc.)
Operation condition: gasification chamber, 350° C.
Column temperature: 190° to 200° C.
Column: 3φ×2 m
Flow rate: $N_2$ 45 ml/min

EXAMPLE 1

Preparation of phospholipid-linked glycosaminoglycan by limited oxidation of reducing terminal group
(1) Preparation of reducing terminal group-limitedly oxidized glycosaminoglycan
  1) Preparation of reducing terminal residue-cleaved hyaluronic acid
  A 2,000 mg portion of hyaluronic acid (HA1; MW, 10,000; cockscomb origin) was dissolved in 200 ml of 0.05M borate buffer (pH 8.3). After adding 182 mg of sodium boron hydride, the resulting mixture was incubated at room temperature for 5 hours to effect the reaction. The reaction mixture was adjusted to pH 4.5 with acetic acid and then mixed with ethanol to form a precipitate. The thus-obtained precipitate was washed with ethanol to give 1,800 mg of reducing terminal residue-cleaved hyaluronic acid (R-HA1; lot No. 100).
  2) Preparation of reducing terminal group-limitedly oxidized hyaluronic acid
  A 1,700 mg portion of R-HA1 (lot No. 100) was dissolved in 250 ml of 40 mM imidazole (pH 6.5). After adding 139.96 mg of sodium periodate at 0° C., the resulting mixture was incubated at the same temperature for 1 hour to effect the reaction. Ethanol was added to the reaction mixture to form a precipitate. The thus-obtained precipitate was washed with ethanol to give 1,600 mg of reducing terminal group-limitedly oxidized hyaluronic acid (O-HA; lot No. 200).
  3) Preparation of other reducing terminal group-limitedly oxidized glycosaminoglycans (O-GAG)
  Reducing terminal residue-cleaved glycosaminoglycans (R-GAG) were prepared according to the above procedure 1) under the conditions shown in Table E, using each of the following starting materials: hyaluronic acid (HA5; MW, 50,000: HA15; MW, 150,000: cockscomb origin), chondroitin (CH; MW, 15,000; sulfuric acid-removed product from chondroitin sulfate A with acidic methanol solution), chondroitin sulfate C (CS (S1); MW, 10,000: CS (S3); MW, 30,000: CS (S6); MW, 60,000: shark cartilage origin), chondroitin sulfate A (CS (W); MW, 30,000: shark cartilage origin), dermatan sulfate (DS; MW, 15,000; swine skin origin), heparin (Hep; MW, 15,000; swine small intestine origin), heparan sulfate (HS; MW, 15,000; bovine kidney origin) and keratan sulfate (KS; MW, 15,000; bovine cornea origin). The thus obtained R-GAG samples were subjected to the above procedure 2) under the conditions shown in Table F to produce reducing terminal group-limitedly oxidized glycosaminoglycans (O-GAG).

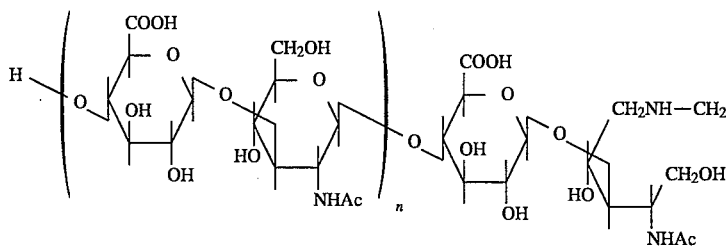

and

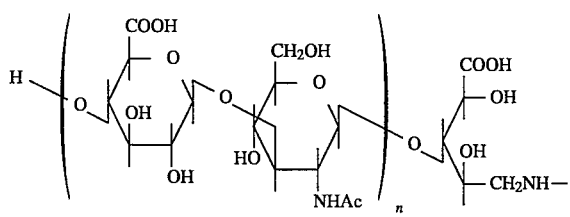

n: average 24

TABLE E

| Lot No. | Product | Reaction condition GAG/NaBH$_4$ (mg/mg) | Yield (mg) |
| --- | --- | --- | --- |
| 100-2 | R-HA5 | 5000/94.58 | 4720 |
| 100-3 | R-HA15 | 1000/6.31 | 971 |
| 101 | R-CH | 1000/63.05 | 867 |
| 102 | R-CS (S1) | 1000/94.58 | 880 |
| 102-2 | R-CS (S3) | 1000/31.50 | 897 |
| 102-3 | R-CS (S6) | 1000/15.76 | 869 |
| 103 | R-CS (W) | 1000/31.50 | 823 |
| 104 | R-DS | 150/9.46 | 130 |
| 105 | R-Hep | 1000/63.05 | 772 |
| 106 | R-HS | 40/2.55 | 35 |
| 107 | R-KS | 20/1.28 | 14.6 |

TABLE F

| Lot No. | Product | Reaction condition R-GAG/NaIO$_4$ (mg/mg) | Yield (mg) |
| --- | --- | --- | --- |
| 200-2 | O-HA5 | 4500/77.0 | 4310 |
| 200-3 | O-HA15 | 900/5.14 | 815 |
| 201 | O-CH | 800/45.65 | 766 |
| 202 | O-CS (S1) | 800/68.48 | 715 |
| 202-2 | O-CS (S3) | 800/22.83 | 774 |
| 202-3 | O-CS (S6) | 800/11.41 | 699 |
| 203 | O-CS (W) | 800/22.83 | 697 |
| 204 | O-DS | 100/5.71 | 82 |
| 205 | O-Hep | 700/39.95 | 666 |
| 206 | O-HS | 30/1.71 | 22 |
| 207 | O-KS | 10/0.57 | 7 |

(2) Preparation of L-(α-phosphatidyl)ethanolamine dipalmitoyl-linked glycosaminoglycan (GAG-PPEADP)

1) Preparation of L-(α-phosphatidyl)ethanolamine dipalmitoyl-linked hyaluronic acid

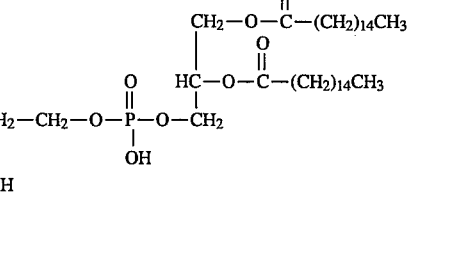

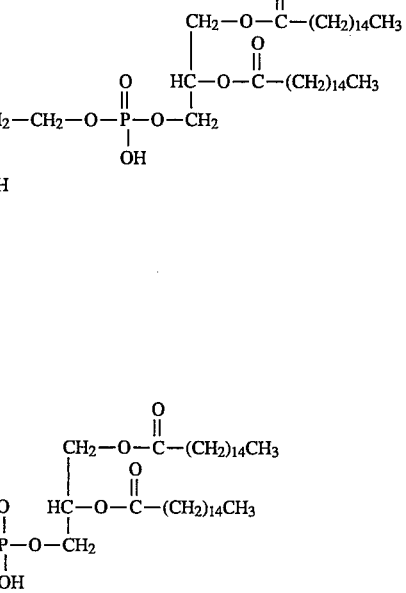

1,000 mg of lot No. 200 O-HA was dissolved in 100 ml of 0.05M phosphate buffer (pH 7.0) and 69.2 ml of a chloroform/methanol solvent system (2:1) containing L-(α-phosphatidyl)ethanoyl dipalmitoyl (PPEADP) (1 mg/ml) was added thereto. The resulting mixture was further mixed with methanol to make the mixture into a uniform solution, and the solution was incubated at 50° C. for 1 hour. After adding 251 mg of sodium cyanoboron hydride to the resulting reaction mixture, incubation was continued at 50° C. for 2 hours, followed by concentration under a reduced pressure. To the concentrate was added five volumes of acetic acid-saturated ethanol to form a precipitate and the precipitate was recovered by filtration. The thus-obtained precipitate was dissolved in 0.3M ammonium chloride solution, applied to a hydrophobic chromatographic column (TSK gel Phenyl Toyopearl 650M; 400 ml), washed thoroughly with 0.3M ammonium chloride solution and then eluted with 30% methanol aqueous solution. The reaction product of interest was found in the 30% methanol fraction, while unreacted HA1 was found in the unabsorbed and washed fractions. The 30% methanol-eluted fraction was concentrated under a reduced pressure, desalted by dialysis and then freeze-dried to obtain white powder of lot No. 300.

Yield: 40 mg

PPEADP content: 6.21%

Hyaluronic acid content: 62.12%

Hydrophobic chromatogram: Shown in FIG. 1

Hydrophobic chromatography was carried out under the following conditions.

Column: TSK gel Phenyl 5 PW (7.5φ×7.5 cm)

Solvent: 0–5 min, 0.3M ammonium chloride solution

5–50 min, 30% methanol solution

Flow rate: 0.5 ml/min

Pressure: 7 kg/0.5 cm$^2$

Fraction volume: 1 ml/tube

Detection: OD$_{220}$ nm

Sample: 100 μl (1 mg/ml solution in 0.3M ammonium chloride)

Preparation of other phospholipid-linked glycosaminoglycans

Phospholipid-linked glycosaminoglycans were prepared in accordance with the above procedure (2)-1) from the O-GAG samples shown in Table F and PPEADP under conditions shown in Table G. Results of the analysis of the thus-obtained products are shown in Table G.

TABLE G

| Lot No. | Product | Reaction condition O-GAG/ PPEADP/ NaBH$_3$CN | Yield (mg) | PPEADP (%) | GAG (%) |
|---|---|---|---|---|---|
| 300-2 | R-HA5-PPEADP | 1000/13.84/5.03 | 42 | 1.33 | 63.43 |
| 300-3 | R-HA15-PPEADP | 700/3.23/1.17 | 35 | 0.46 | 63.35 |
| 301 | CH-PPEADP | 700/32.29/11.73 | 30 | 4.27 | 59.10 |
| 302 | CS(S1)-PPEADP | 700/48.44/17.60 | 36 | 5.89 | 63.04 |
| 302-2 | CS(S3)-PPEADP | 700/16.15/5.89 | 29 | 2.22 | 65.52 |
| 302-3 | CS(S6)-PPEADP | 500/5.77/2.09 | 20 | 1.07 | 67.13 |
| 303 | CS(W)-PPEADP | 500/11.53/4.19 | 22 | 2.23 | 67.48 |
| 304 | DS-PPEADP | 50/2.31/0.84 | 3.7 | 4.21 | 66.10 |
| 305 | Hep-PPEADP | 500/23.07/8.38 | 3.8 | 4.30 | 74.65 |
| 306 | HS-PPEADP | 20/0.92/0.34 | 3.3 | 4.09 | 68.40 |
| 307 | KS-PPEADP | 7/0.33/0.12 | 0.5 | 3.97 | 66.24 |

EXAMPLE 2

Preparation Of phospholipid-linked glycosaminoglycan by lactonization of reducing terminal group (1) Preparation of reducing terminal group-oxidized glycosaminoglycan 1) Preparation of reducing terminal group-oxidized hyaluronic acid 500 mg of hyaluronic acid (HA1; MW, 10,000; cockscomb origin) was dissolved in 10 ml of water, and the solution was mixed with 5 ml methanol solution of 0.1M iodine and incubated at room temperature for 6 hours to effect the reaction. To the resulting reaction mixture was added about 5 ml of 0.1N potassium hydroxide to decolor free iodine molecules. Potassium acetate-saturated ethanol was added to the resulting solution to form a precipitate and the precipitated product was collected by filtration, washed thoroughly with ethanol and then dried under a reduced pressure. Thus, 423 mg of reducing terminal group-oxidized hyaluronic acid (lot No. 400) was obtained. Reducing sugar was not detected in the product when checked by Somogyi-Nelson method.

2) Preparation of reducing terminal group-lactonized hyaluronic acid 400 mg of the lot No. 400 reducing terminal group-oxidized hyaluronic acid was dissolved in 10 ml of water, and the solution was passed through 50 ml of a column of a strongly acidic ion exchange resin (Dowex 50(H$^+$)) spending 1 hour. Thus, a solution containing 390 mg of reducing terminus-lactonized hyaluronic acid was obtained. Reducing sugar was not detected in the solution when checked by Somogyi-Nelson method.

The thus-obtained solution was neutralized with tri-n-butylamine and subsequently freeze-dried to obtain 400 mg of tri-n-butylamine salt of reducing terminus-lactonized hyaluronic acid (lot No. 500).

3) Preparation of other reducing terminus-lactonized glycosaminoglycans

Reducing terminal group-oxidized glycosaminoglycans were prepared according to the above procedure 1) under conditions shown in Table H, using each of the following starting materials: chondroitin (CH; MW, 15,000), chondroitin sulfate C (CS (S1); MW, 10,000: CS (S3); MW, 30,000: and CS (S6); MW, 60,000), dermatan sulfate (DS; MW, 15,000), heparin (Hep; MW, 15,000) and heparan sulfate (HS; MW, 15,000). The thus-obtained samples were subjected to the above procedure 2) under conditions shown in Table I to produce reducing terminal group-lactonized glycosaminoglycans.

TABLE H

| Lot No. | Product | Reaction condition GAG/0.1M I$_2$/0.1N KOH (mg/ml/ml) | Yield (%) | Somogyi-Nelson |
|---|---|---|---|---|
| 401 | CH-COOK | 1000/13.4/13.4 | 828 | — |
| 402 | CS(S1)-COOK | 1000/19.8/19.8 | 901 | — |
| 402-2 | CS(S3)-COOK | 1000/3.3/3.3 | 895 | — |
| 402-3 | CS(S6)-COOK | 1000/4.95/4.95 | 913 | — |
| 404 | DS-COOK | 100/0.67/0.67 | 91 | — |
| 405 | Hep-COOK | 1000/6.7/6.7 | 902 | — |
| 406 | HS-COOK | 100/1.34/1.34 | 88 | — |

*Somogyi-Nelson: presence (+) or absence (−) of reducing sugar determined by Somogyi-Nelson method.

TABLE I

| Lot No. | Product | Reaction condition GAG-COOK/ Dowex 50 (H$^+$) (mg/ml) | Yield (%) | Somogyi-Nelson |
|---|---|---|---|---|
| 501 | CH-lactone | 800/400 | 780 | — |
| 502 | CS(S1)-lactone | 900/450 | 805 | — |
| 502-2 | CS(S3)-lactone | 800/400 | 850 | — |
| 502-3 | CS(S6)-lactone | 900/450 | 887 | — |
| 504 | DS-lactone | 90/100 | 96 | — |
| 505 | Hep-lactone | 900/400 | 946 | — |
| 506 | HS-lactone | 80/40 | 72 | — |

*Somogyi-Nelson: presence (+) or absence (−) of reducing sugar determined by Somogyi-Nelson method.

(2) Preparation of L-(α-phosphatidyl)ethanolamine dipalmitoyl-linked glycosaminoglycan (GAG-PPEADP)

Preparation of L-(α-phosphatidyl)ethanolamine dipalmitoyl-linked hyaluronic acid

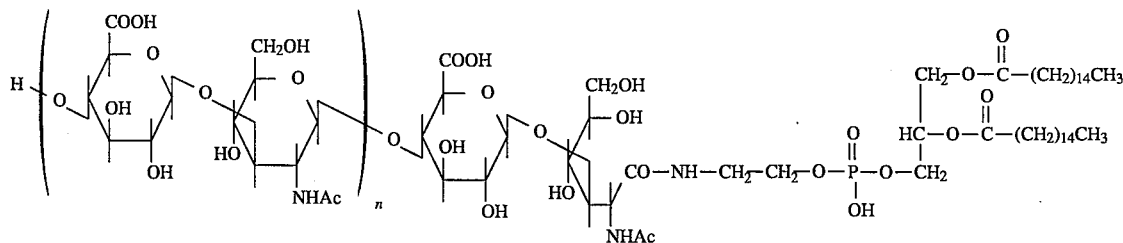

and

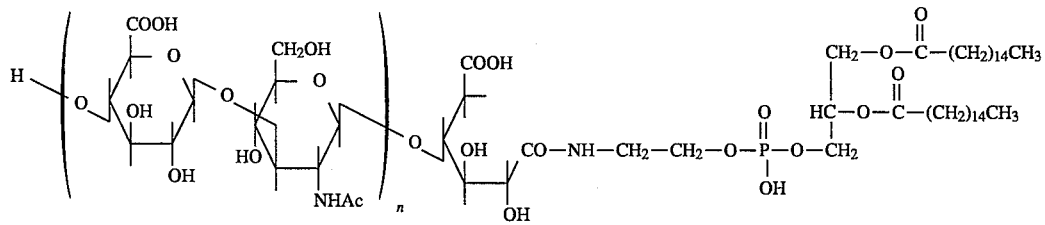

n: average 25

400 mg of lot No. 500 reducing terminus-lactonized hyaluronic acid was dissolved in 200 ml of dimethylformamide and 27.6 mg of PPEADP dissolved in chloroform was added thereto. The resulting mixture was incubated at 70° C. for 2 hours. After removing chloroform from the reaction mixture by distillation, excess volume of sodium acetate aqueous solution was added to the residue to make the reaction product into sodium salt. Sodium acetate-saturated ethanol was added thereto to form a precipitate and the thus-formed precipitate was collected by filtration. The precipitate was dissolved in 0.3M ammonium acetate solution and subjected to purification in accordance with the procedure of Example 1-(2) to obtain 36 mg of the desired product (lot No. 600).

Phosphorus content: 0.30%

PPEADP content: 6.44%

Hyaluronic acid content: 82.37%

Figure 2:
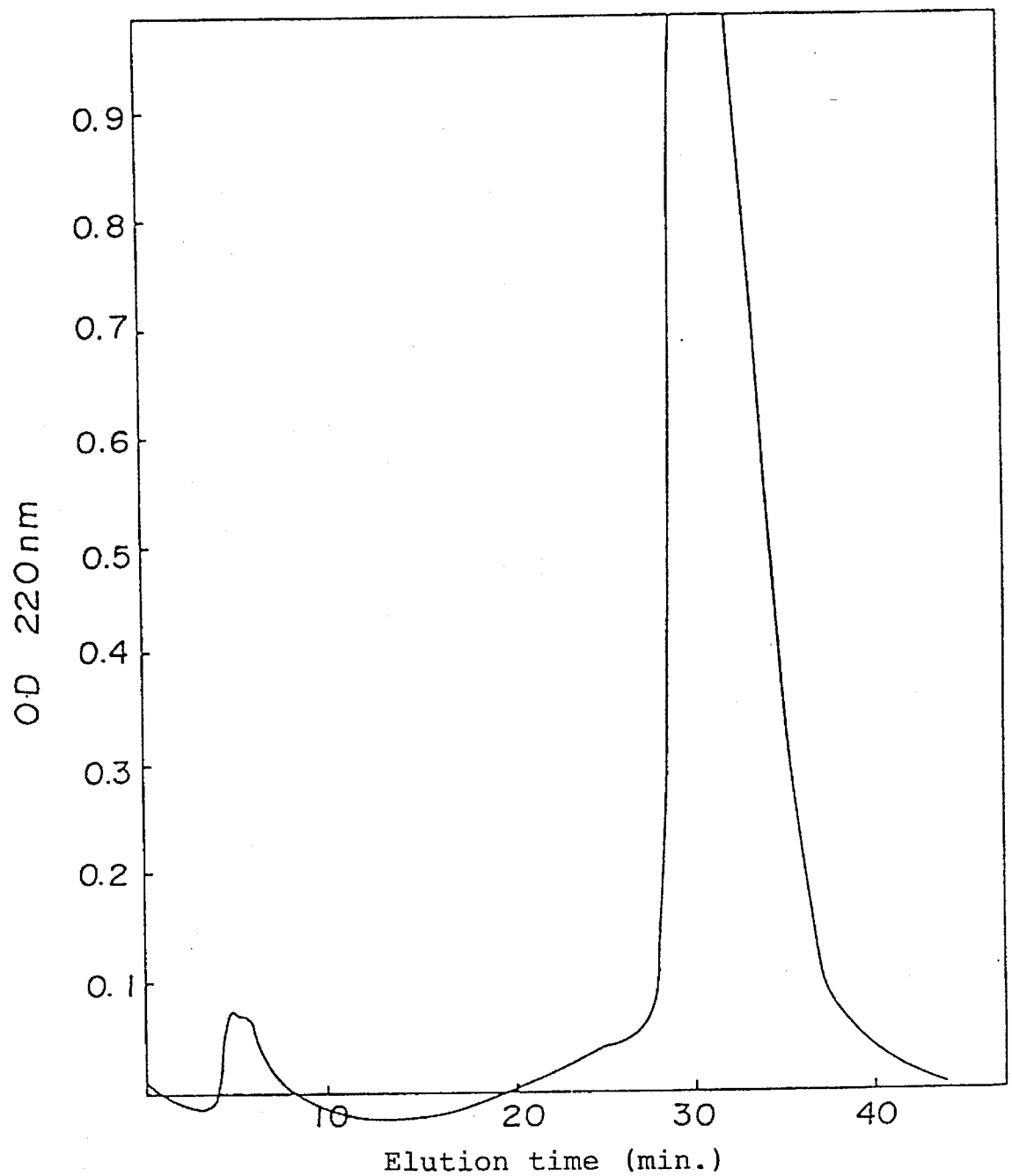

Hydrophobic chromatogram: Shown in FIG. 2. Measuring conditions are the same as described above.

(2) Preparation of other L-(α-phosphatidyl)ethanolamine dipalmitoyl-linked glycosaminoglycans These samples were prepared from the reducing terminus-lactonized glycosaminoglycans shown in Table I and PPEADP in accordance with the above procedure (2)-1) under conditions shown in Table J. Results of the analysis of the thus-obtained products are shown in Table K.

TABLE J

| Lot No. | Product | Reaction condition GAG-lactone/PPEADP (mg/mg) |
|---|---|---|
| 601 | CH-PPEADP | 700/32.3 |
| 602 | CS(S1)-PPEADP | 800/55.4 |
| 602-2 | CS(S3)-PPEADP | 400/9.26 |
| 602-3 | CS(S6)-PPEADP | 800/9.00 |
| 604 | DS-PPEADP | 90/4.15 |
| 605 | Hep-PPEADP | 800/36.91 |
| 606 | HS-PPEADP | 70/3.31 |

TABLE K

| Lot No. | Product | Yield (mg) | PPEADP (%) | GAG (%) |
|---|---|---|---|---|
| 601 | CH-PPEADP | 70.2 | 4.30 | 90.90 |
| 602 | CS(S1)-PPEADP | 88.0 | 6.41 | 85.17 |
| 602-2 | CS(S3)-PPEADP | 20 | 2.01 | 89.70 |
| 602-3 | CS(S6)-PPEADP | 56.2 | 1.08 | 92.00 |
| 604 | DS-PPEADP | 4.5 | 4.00 | 90.66 |
| 605 | Hep-PPEADP | 24 | 4.11 | 90.01 |
| 606 | HS-PPEADP | 5.74 | 4.22 | 88.21 |

(3) Production of phosphotidylserin stearoylpalmitoyl-linked chondroitin sulfate C

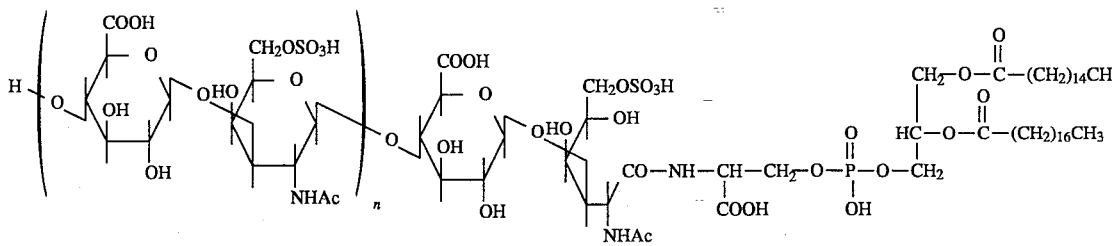

and

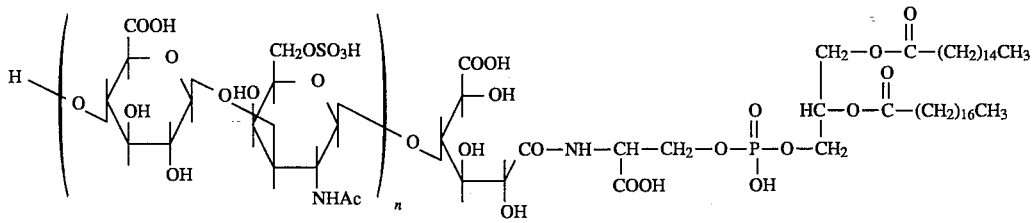

n: average 60

400 mg of lot No. 502-2 reducing terminus-lactonized chondroitin sulfate C was dissolved in 200 ml of diethylformamide and 9 mg of phosphatidylserin stearate palmitate in chloroform was added thereto. The resulting mixture was incubated at 70° C. for 2 hours. After removing chloroform from the reaction mixture by distillation, excess volume of sodium acetate aqueous solution was added to the residue to make the reaction product into sodium salt. Sodium acetate-saturated ethanol was added thereto to form a precipitate and the thus-formed precipitate was collected by filtration. The precipitate was dissolved in 0.3M ammonium chloride solution and then subjected to purification in accordance with the procedure of Example 1-(2) to obtain 20.8 mg of phosphatidylserin stearoylpalmitoyl-linked chondroitin sulfate C (lot No. 700-2).

Phosphorus content: 0.10%

Chondroitin sulfate C content: 86.15%

Figure 3:
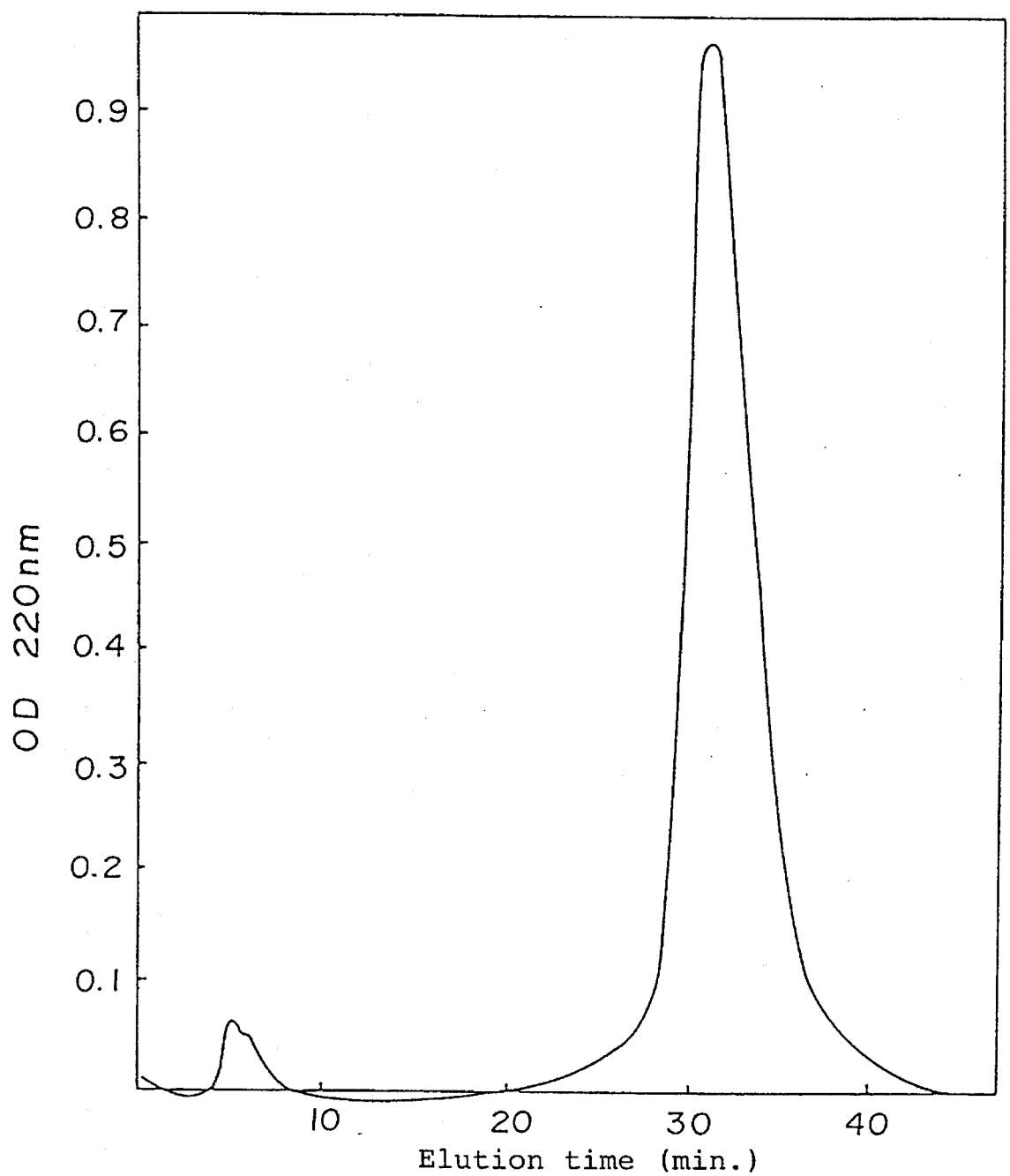

Hydrophobic chromatogram: Shown in FIG. 3. Measuring conditions are the same as described above.

EXAMPLE 3

Preparation of phospholipid- or lipid-linked glycosaminoglycan by amination of reducing terminal group (1) Preparation of reducing terminal group-aminated glycosaminoglycan 1) Preparation of reducing terminus-aminated chondroitin sulfate C (CS(S3))

100 mg of reducing terminal group-limitedly oxidized chondroitin sulfate C (lot No. 202-2) was dissolved in 50 ml of 0.05M phosphate buffer (pH 7.0), and the solution was mixed with 24 mg of ethylenediamine hydrochloride. After incubating the resulting mixture at 50° C. for 30 minutes, 20 mg of sodium cyanoboron hydride was added to the reaction mixture and the incubation was continued at 50° C. for 2 hours to complete the reaction. Sodium acetate-saturated ethanol was added to the resulting reaction mixture to precipitate the reaction product which was then collected by filtration. The precipitate was dissolved in water and absorbed to 50 ml of DEAE-ion exchange resin, followed by gradient elution with 0.1M–1M sodium chloride aqueous solution. The reducing terminus-aminated chondroitin sulfate C was eluted with 0.4M sodium chloride, while free chondroitin sulfate C was eluted with 0.75M sodium chloride. The 0.4M sodium chloride fraction was desalted by dialysis and then freeze-dried to obtain 80 mg of reducing terminal group-aminated chondroitin sulfate C (lot No. 802-2).

2) Preparation of reducing terminus-aminated heparin (Hep)

The above procedure was repeated except that 100 mg of lot No. 205 reducing terminal group-limitedly oxidized heparin was used. Thus, 77 mg of reducing terminus-aminated heparin (lot No. 805) was obtained.

(2) Preparation of succinic acid derivative of lipid

1) Preparation of succinic acid ester of glycerol monostearate 10.74 g of glycerol monostearate was dissolved in 200 ml of benzene containing 3 ml of pyridine. After adding 6 g of succinic anhydride, the resulting mixture was subjected to reflux for 6 hours. The resulting reaction mixture was concentrated under a reduced pressure, and the precipitate thus formed was subjected to recrystallization from acetone to obtain 8.2 g of succinic acid ester of glycerol monostearate.

2) Preparation of active ester from succinic acid ester of glycerol monostearate with N-hydroxysuccinic acid imide 8 g of the ester obtained in the above procedure 1) was dissolved in benzene, and the solution was mixed with 2 g of N-hydroxysuccinic acid imide and 10 g of dicyclohexylcarbodiimide. After incubating the resulting mixture at room temperature for 20 hours, the reaction mixture was concentrated under a reduced pressure to obtain precipitate of the reaction product. The precipitate was recrystallized from a benzene/n-hexane solvent system to obtain 7.4 g of the desired active ester (lot No. GMS-1).

(3) Preparation of glycerol monostearate-linked chondroitin sulfate C $$\left( \begin{array}{c} \text{COOH} \\ \text{H} \\ \text{O} \\ \text{OH} \\ \text{OH} \end{array} \begin{array}{c} \text{CH}_2\text{OSO}_3\text{H} \\ \text{O} \\ \text{OHO} \\ \text{NHAc} \end{array} \right)_n \begin{array}{c} \text{COOH} \\ \text{OH} \\ \text{O} \\ \text{OH} \\ \text{CH}_2-\text{NH}-(\text{CH}_2)_2-\text{NHCO}-(\text{CH}_2)_2-\text{COO}-\text{CH}_2 \end{array} \begin{array}{c} \text{CH}_2\text{OH} \\ \text{O} \\ \text{HC}-\text{O}-\overset{\text{O}}{\overset{\|}{\text{C}}}-(\text{CH}_2)_{16}\text{CH}_3 \end{array}$$

n: average 60

In 5 ml of water was dissolved 80 mg of the lot No. 802-2 reducing terminus-aminated chondroitin sulfate C. The resulting solution was mixed with 6.95 mg of the lot No. GMS-1 active ester dissolved in dimethylformamide. After incubating the resulting mixture at room temperature for 20 hours, the reaction mixture was mixed with sodium acetate-saturated ethanol to precipitate the reaction product which was subsequently collected by filtration. The thus-collected precipitate was dissolved in 0.3M ammonium chloride aqueous solution and the resulting solution was subjected to purification in the same manner as in the procedure of Example 1-(2)-1) to obtain 38 mg of the desired compound (lot No. 902-2).

Stearic acid content: 0.86%

Chondroitin sulfate C content: 98.2%

(4) Preparation of succinic acid derivative of phospholipid

1) Preparation of succinic acid ester of lysolecithin

In 200 ml of chloroform was dissolved 495 mg of lysolecithin of the following formula.

$$\begin{array}{c} \text{CH}_2\text{OCO}-(\text{CH}_2)_{14}-\text{CH}_3 \\ | \\ \text{HOCH} \\ | \\ \text{CH}_2\text{OPO}(\text{O}^-)\text{OCH}_2\text{CH}_2\text{N}^+(\text{CH}_3)_3 \end{array}$$

To the resulting solution were added 100 mg of succinic anhydride and 79 mg of pyridine. After incubating the mixture at room temperature for 20 hours, the reaction mixture was concentrated under a reduced pressure to form a precipitate. The thus-formed precipitate was recrystallized from acetone to obtain a succinic acid ester of lysolecithin.

2) Preparation of active ester from succinic acid ester of lysolecithin with N-hydroxysuccinic acid imide 288.5 mg of the ester obtained above was dissolved in dimethylformamide, and the solution was mixed with 57.5 mg of N-hydroxysuccinic acid imide and 103 mg of dicyclohexylcarbodiimide. After incubating the thus-prepared mixture at room temperature for 20 hours, precipitated materials were removed from the resulting reaction mixture to obtain a dimethylformamide solution of the desired active ester.

(5) Preparation of lysolecithin-linked glycosaminoglycan

5) Preparation of lysolecithin-linked chondroitin sulfate C $$\left( \begin{array}{c} \text{COOH} \\ \text{H} \\ \text{O} \\ \text{OH} \\ \text{OH} \end{array} \begin{array}{c} \text{CH}_2\text{OSO}_3\text{H} \\ \text{O} \\ \text{OHO} \\ \text{NHAc} \end{array} \right)_n \begin{array}{c} \text{COOH} \\ \text{OH} \\ \text{O} \\ \text{OH} \\ \text{CH}_2-\text{NH} + (\text{CH}_2)_{\overline{2}}\text{NHCO} + (\text{CH}_2)_{\overline{2}}\text{COO}-\text{CH} \end{array} \begin{array}{c} \text{CH}_2\text{OCO}(\text{CH}_2)_{14}\text{CH}_3 \\ | \\ \text{O} \\ | \overset{\|}{\text{P}} \\ \text{CH}_2\text{O}-\text{P}-\text{O}-\text{CH}_2-\text{CH}_2-\text{N}(\text{CH}_3)_3^+ \\ | \\ \text{O}^- \end{array}$$

n: average 60

The dimethylformamide solution of the active ester obtained in the above procedure (4)-2) was mixed with an aqueous solution of 1 g of the lot No. 802-2 reducing terminus-aminated chondroitin sulfate C, and the mixture was incubated at room temperature for 20 hours to effect the reaction. Purification of the reaction product was carried out by hydrophobic chromatography in accordance with the procedure of Example 1.

Yield: 0.52 g

Phosphorus content: 0.105%

Lysolecithin content: 1.96%

Chondroitin sulfate content: 98.04%

Sulfur content: 5.78%

(6) Preparation of glycerol distearate-linked chondroitin sulfate C

An active ester of a succinic acid ester of glycerol distearate was prepared according to the above procedure (2)-2) (lot No. GDS-2). This was allowed to react with reducing terminus-aminated chondroitin sulfate C (lot No. 802-2) obtained in the above procedure (1)-1) in accordance with the above procedure (3), followed by purification. Thus, 27 mg of the desired compound was obtained (lot No. 904).

EXAMPLE 4

Preparation of phospholipid-linked glycosaminoglycan using condensing agent (1) Preparation of L-(α-phosphatidyl)ethanolamine dipalmitoyl-linked chondroitin sulfate C

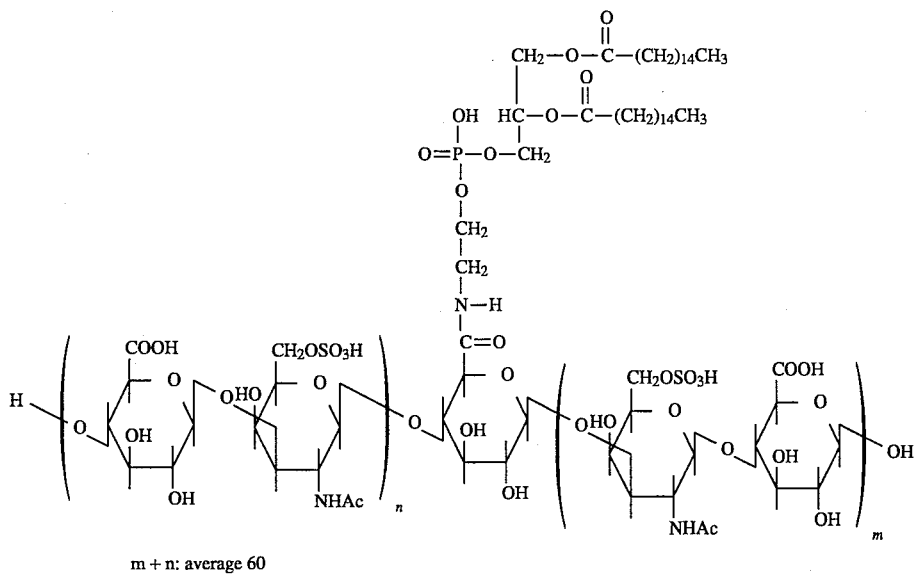

m + n: average 60

400 mg of tri-n-butylamine salt of chondroitin sulfate C (CS(S3)) was dissolved in 100 ml of dimethylformamide. To the resulting solution were added 6.92 mg of PPEADP dissolved in chloroform and 38.4 mg of 1-ethyl- 3-(3-dimethylaminopropyl)carbodiimide hydrochloride. The resulting mixture was incubated at room temperature for 20 hours to effect the reaction. After concentrating under a reduced pressure, excess volume of sodium acetate aqueous solution was added to the concentrate to make the reaction product into sodium salt. Ethanol was added thereto to precipitate the salt and the thus-formed precipitate was collected by filtration. The precipitate was dissolved in 0.3M ammonium chloride solution and then subjected to purification in accordance with the procedure of Example 1-(2)-1). Thus, 63 mg of the desired compound (lot No. 1002-2) was obtained.

Phosphorus content: 0.099%

PPEADP content: 2.25%

Chondroitin sulfate C content: 96.61%

Figure 4:
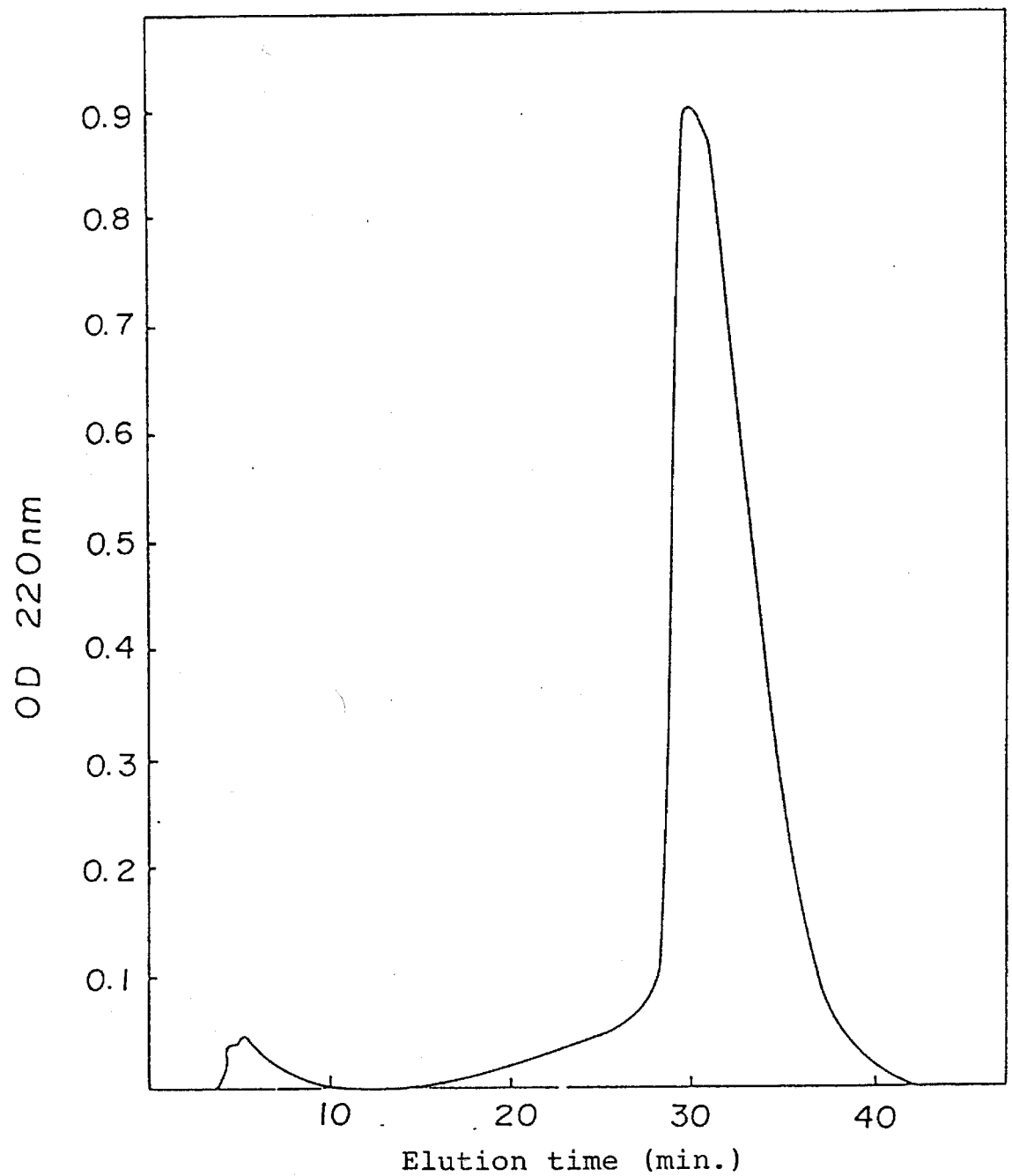

Hydrophobic chromatogram: Shown in FIG. 4 Measuring conditions are the same as described above.

(2) Preparation of other L-(α-phosphatidyl)ethanolamine dipalmitoyl-linked glycosaminoglycans (GAG-PPEADP)

Phospholipid-linked glycosaminoglycans were prepared from various glycosaminoglycans and PPEADP in accordance with the above procedure (1) under conditions shown in Table L. Results of the analysis of the thus-obtained products are shown in Table M.

TABLE L

| Lot No. | Product | Reaction condition GAG*[1]/PPEADP/WSC (mg/mg/mg) |
|---|---|---|
| 1000 | HA1-PPEADP | 420/20.76/103 |
| 1001 | CH-PPEADP | 420/13.84/68.8 |
| 1002-1 | CS(S1)-PPEADP | 400/20.76/103 |
| 1002-3 | CS(S6)-PPEADP | 400/3.46/17.2 |
| 1003 | CS(2)-PPEADP | 400/6.92/34.3 |
| 1004 | DS-PPEADP | 40/1.38/6.88 |
| 1005 | Hep-PPEADP | 400/13.8/68.8 |
| 1006 | HS-PPEADP | 13/0.46/2.3 |

TABLE L-continued

| Lot No. | Product | Reaction condition GAG*[1]/PPEADP/WSC (mg/mg/mg) |
|---|---|---|

*[1]tri-n-butylamine salt

TABLE M

| Lot No. | Product | Yield (mg) | PPEADP (%) | GAG (%) |
|---|---|---|---|---|
| 1000 | HA1-PPEADP | 28 | 6.21 | 90.05 |
| 1001 | CH-PPEADP | 25.8 | 4.01 | 88.64 |
| 1002-1 | CS(S1)-PPEADP | 51.9 | 5.28 | 92.40 |
| 1002-3 | CS(S6)-PPEADP | 42.2 | 1.04 | 97.81 |
| 1003 | CS(W)-PPEADP | 41.9 | 2.17 | 96.62 |
| 1004 | DS-PPEADP | 29 | 4.41 | 89.12 |
| 1005 | Hep-PPEADP | 101.3 | 4.04 | 90.03 |
| 1006 | HS-PPEADP | 1.2 | 4.00 | 88.22 |

EXAMPLE 5

Preparation of phospholipid-linked glycosaminoglycan by glycosaminoglycan-activation method (1) Preparation of L-(α-phosphatidyl)ethanolamine dipalmitoyl-linked chondroitin sulfate C

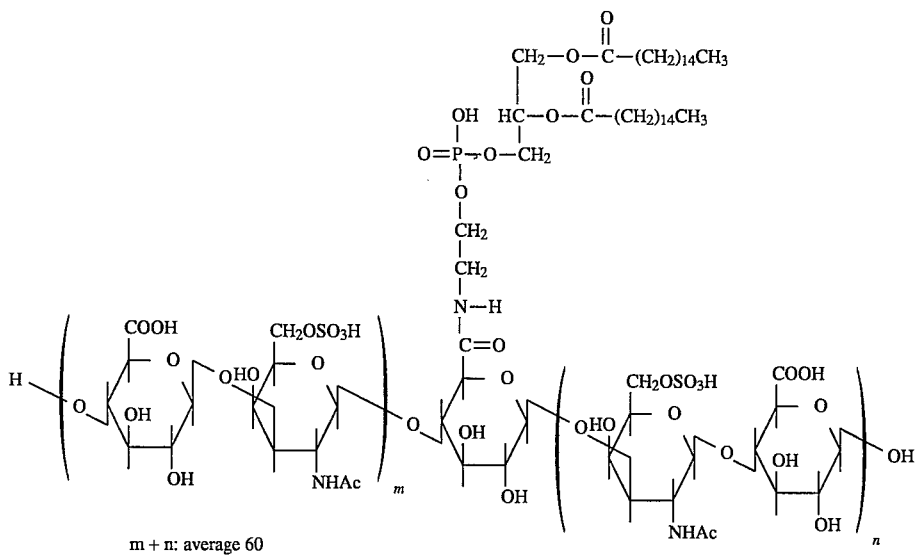

400 mg of tri-n-butylamine salt of chondroitin sulfate C (CS(S3)) was dissolved in 300 ml of DMF. To the resulting solution were added 9.9 mg of N-hydroxysuccinimide and 20.6 mg of dicyclohexylcarbodiimide. The resulting mixture was incubated at room temperature for 20 hours. Excess volume of sodium acetate aqueous solution was added to the resulting reaction mixture to make the reaction product into sodium salt, followed by the addition of ethanol to collect formed precipitate by filtration. The thus-collected precipitate was immediately dissolved in 30 ml of water, and the solution was mixed with 6.92 g of PPEADP dissolved in chloroform. Dimethylformamide was further added thereto to obtain a uniform solution. After incubating the thus-obtained solution at room temperature for 6 hours, the reaction mixture was concentrated under a reduced pressure and then mixed with acetic acid-saturated ethanol to form a precipitate. Thereafter, the thus-formed precipitate was collected by filtration and dissolved in 0.3M ammonium acetate solution followed by purification in accordance with the procedure of Example 1-(2)-1). Thus, 29.7 mg of the desired compound (lot No. 1102-2) was obtained.

Phosphorus content: 0. 100%

PPEADP content: 2.16%

Chondroitin sulfate C content: 95.68%

Figure 5:
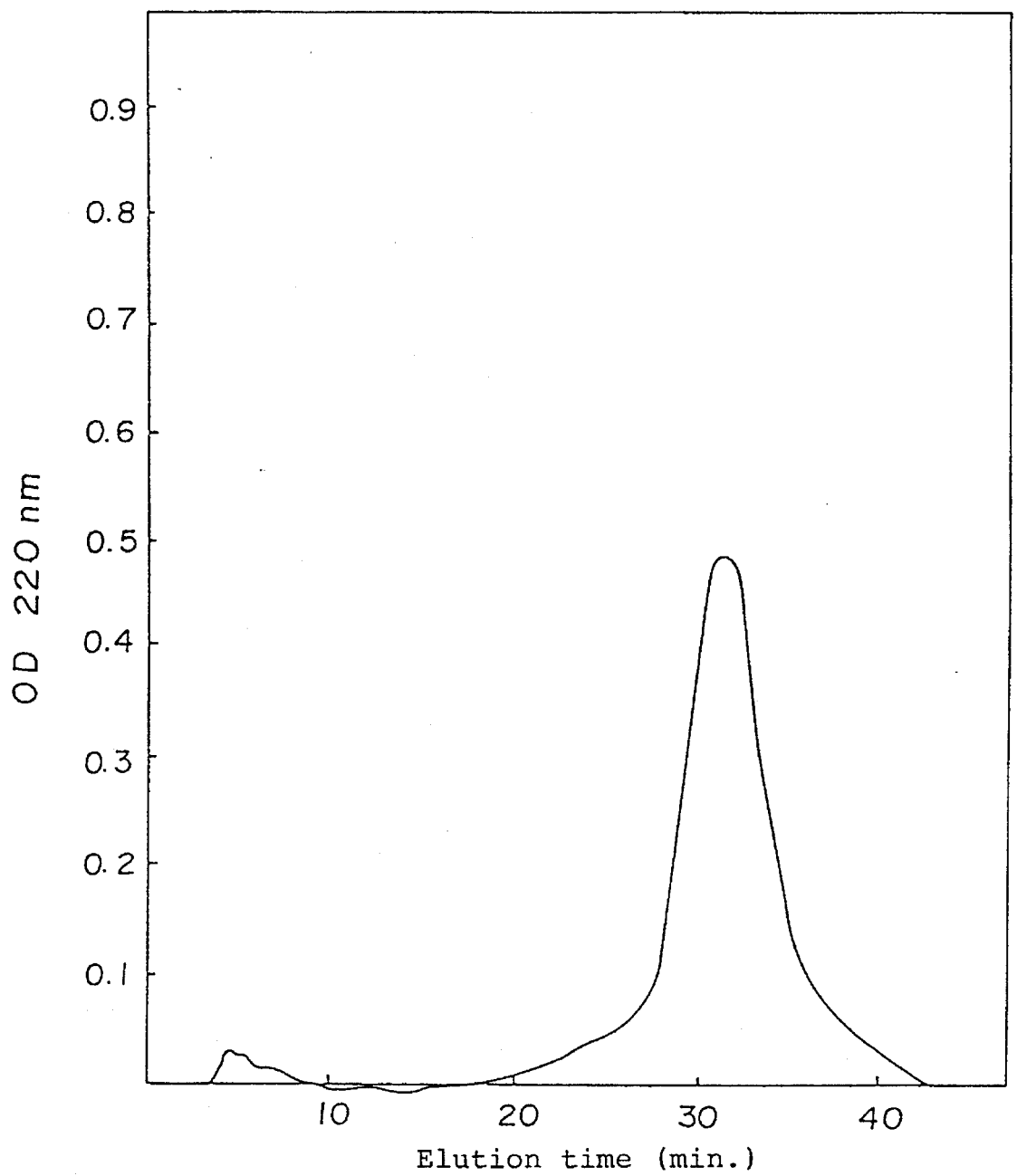

Hydrophobic chromatogram: Shown in FIG. 5. Measuring conditions are the same as described above.

(2) Preparation of L-(α-phosphatidyl)ethanolamine dipalmitoyl-linked chondroitin polysulfate.

1 g of tri-n-butylamine salt (sulfur content, 13.0%; molecular weight, 10,000) of chondroitin polysulfate (CSP(II)) was dissolved in 50 ml of dimethylformamide. To the resulting solution were added 1770 mg of N-hydroxysuccinimide and 318 mg of dicyclohexylcarbodiimide. The resulting mixture was incubated overnight at 4° C. Thereafter, 10 ml of water was added to the reaction mixture and the mixture was further allowed to react at room temperature for 15 minutes. After removing formed precipitate, the resulting solution was mixed with 69.2 g of phosphatidyl ethanolamine dipalmitoyl (PPEADP) dissolved in chloroform, and the mixture was allowed to react at room temperature for 6 hours. The resulting reaction mixture was concentrated under a reduced pressure and then mixed with sodium acetate-saturated ethanol to form a precipitate. Thereafter, the thus-formed precipitate was collected by filtration and dissolved in 0.3M ammonium acetate solution, followed by purification in accordance with the procedure of Example 1-(2)-1). Thus, 67 mg of the desired compound (lot No. 1108) was obtained.

Phosphorus content: 0.291%

PPEADP content: 6.5%

Chondroitin polysulfate content: 92.8%

Sulfur content: 12.05%

Figure 6:
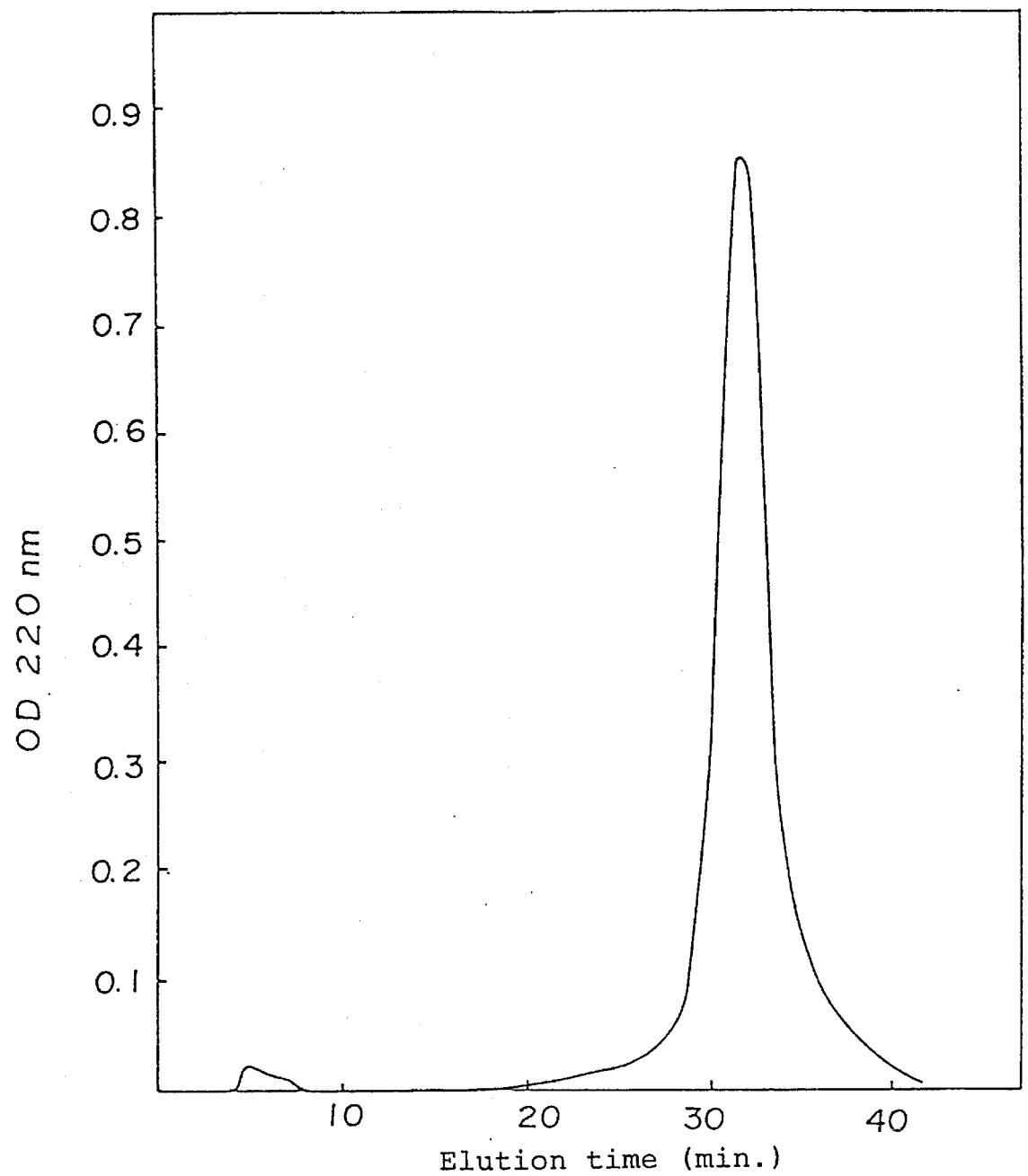

Hydrophobic chromatogram: Shown in FIG. 6. Measuring conditions are the same as described above.

EXAMPLE 6

Adhesion of BHK cells to a phospholipid- or lipid-linked glycosaminoglycan layer laminated on fibronectin-coated inside wall of a culture dish Each well of a 96-well incubation plate was coated with 100 μl of 5 μg/ml solution of bovine serum-derived fibronectin. After washing, each well was further coated with 100 μl of each of the phospholipid- or lipid-linked glycosaminoglycans obtained in Examples 1 to 5, with their concentrations shown in Table N.

Separately, BHK cells (new-born hamster kidney cells) cultured in a dish of 100 mm in diameter were treated with 5 ml of 0.1 mg/ml trypsin solution at 37° C. for 5 minutes. To the thus-treated cells was added 5 ml of 1 mg/ml solution of soy bean trypsin inhibitor in order to inactivate trypsin. Thereafter, the thus-separated cells were collected by centrifugation, washed twice and then made into a single cell suspension with a density of $1\times10^5$ cells/ml.

A 100 μl portion of the thus-obtained single cell suspension ($1\times10^4$ cells) was poured in each well of the incubation plate which had been double-coated with fibronectin and a phospholipid- or lipid-linked glycosaminoglycan as described above. After incubating at 37° C. for 1 hour, cells which did not adhere were washed out, and the remaining adhered cells were fixed with 2% formaldehyde and observed directly under a phase-contrast microscope to count the number of adhered cells.

Table N shows the concentration-depending changes in the number of adhered cells. Each of the data was expressed in terms of a mean value of three or four measurements. Error (standard deviation) in each experiment is also shown.

When free glycosaminoglycans or unlinked lipids were used instead of the phospholipid- or lipid-linked glycosaminoglycans, they showed no cell adhesion-inhibiting effect even at high concentrations.

In Table O, relative adhered cell numbers are semi-quantitatively expressed as "−" for no or little adhesion (0 to less than 10%), "+" for 10 to less than 30%, "++" for 30 to less than 50%, "+++" for 50 to less than 70%, "++++" for 70 to less than 90% and "+++++" for 90 to 100% adhesion.

TABLE N

| Sample (μg/ml) | Lot No. | | | | | |
|---|---|---|---|---|---|---|
| | 302-3 CS(S6)-PPEADP | 600 HA1-PPEADP | 601 CH-PPEADP | 602 CS(S1)-PPEADP | 602-2 CS(S3)-PPEADP | 602-3 CS(S6)-PPEADP |
| 0.1 | | | | | 98.7% ± 0.9% | 98.9% ± 0.9% |
| 0.2 | | | | 87.4% ± 8.8% | 82.4% ± 3.8% | 89.3% ± 0.5% |
| 0.5 | | | | 89.1% ± 15.3% | 49.8% ± 4.6% | 85.0% ± 1.1% |
| 1 | 91.4% ± 6.8% | | | 50.2% ± 5.2% | 44.7% ± 6.8% | 40.0% ± 3.6% |
| 2 | 60.9% ± 4.5% | | 85.0% ± 2.6% | 33.5% ± 6.9% | 35.4% ± 9.5% | 12.7% ± 1.0% |
| 5 | 23.0% ± 0.2% | 73.5% ± 1.3% | 81.6% ± 6.0% | 24.4% ± 0.5% | 4.3% ± 1.3% | 1.6% ± 0.7% |
| 10 | 1.3% ± 1.2% | 72.5% ± 8.8% | 80.5% ± 6.9% | 12.8% ± 2.4% | 2.8% ± 0.4% | 1.3% ± 0.5% |
| 20 | | 29.9% ± 2.6% | 63.8% ± 2.7% | 3.2% ± 1.1% | 0.7% ± 0.1% | 0.0% ± 0.0% |
| 50 | | 3.6% ± 0.5% | 65.5% ± 10.0% | | | |
| 100 | | 0.8% ± 0.1% | 44.4% ± 4.2% | | | |
| 200 | | 0.3% ± 0.2% | 33.8% ± 3.8% | | | |
| 500 | | | | | | |

| Sample (μg/ml) | Lot No. | | | | | |
|---|---|---|---|---|---|---|
| | 604 DS-PPEADP | 605 Hep-PPEADP | 606 HS-PPEADP | 1000 HA1-PPEADP | 1002-2 CS(S3)-PPEADP | 1004 DS-PPEADP | 1005 Hep-PPEADP |
| 0.1 | | | | | | | |
| 0.2 | 85.8% ± 4.6% | | | | | | |
| 0.5 | 80.2% ± 3.6% | | | | | | |
| 1 | − ± − | | | | 88.3% ± 16.6% | | |
| 2 | − ± − | 86.7% ± 1.3% | | | 57.6% ± 4.8% | 99.3% ± 7.8% | |
| 5 | 14.9% ± 2.0% | 76.1% ± 5.4% | 14.9% ± 0.6% | | 19.6% ± 4.4% | 89.9% ± 0.4% | |
| 10 | 6.7% ± 1.2% | 60.5% ± 6.9% | 5.7% ± 0.5% | | 7.5% ± 3.7% | 75.6% ± 4.9% | |
| 20 | 2.4% ± 0.9% | 44.0% ± 5.0% | 2.0% ± 0.3% | 95.6% ± 4.8% | | 65.0% ± 5.7% | 95.3% ± 0.9% |
| 50 | 0.9% ± 0.6% | 46.0% ± 7.5% | 1.3% ± 0.4% | 80.5% ± 5.4% | | 56.2% ± 1.1% | 75.0% ± 12.1% |
| 100 | | 17.3% ± 3.4% | 1.0% ± 0.1% | 73.5% ± 0.6% | | 43.7% ± 4.9% | 55.9% ± 1.1% |
| 200 | | 11.6% ± 2.2% | 0.9% ± 0.0% | 55.0% ± 0.3% | | | 45.1% ± 1.0% |
| 500 | | | | | | | |

EXAMPLE 7

Effect of phospholipid- or lipid-linked glycosaminoglycan for inhibiting cell adhesion of various cultured cell lines by cell adhesion substances The phospholipid- or lipid-linked glycosaminoglycans obtained in Examples 1 to 5 were examined for their effects for inhibiting cell adhesion of various cell lines by cell adhesion substances, using BHK 21 (new-born hamster kidney cell), CEF (arian embryo fibroblast cell), B16F10 (highly metastatic mouse melanoma cell), CHO (Chinese hamster ovarian cell) and baEC (bovine aorta endothelial cell) as the cell lines, and fibronectin (FN), laminin (LN), type I collagen (ColI) and vitronectin (VN) as the cell adhesion substances.

A 5 μg/ml portion of each of fibronectin derived from bovine blood plasma, laminin derived from mouse EHS tumor cell, type I collagen derived from rat thigh and bovine serum-derived vitronectin was coated on a 96-well incubation plate and each of the phospholipid- or lipid-linked glycosaminoglycans obtained in Examples 1 to 5 was further coated in the same manner as in Example 6. Thereafter, a 100 μl portion of a single cell suspension ($1 \times 10^4$ cells) of each of BHK 21, CEF, B16F10, CHO and baEC cells was poured in each well to observe changes in the cell adhesion. As a control, the same procedure was repeated except that the phospholipid- or lipid-linked glycosaminoglycan was not used, and the resulting cell adhesion was expressed as 100%. The results are shown in Table O.

TABLE O

| | | Cells/cell adhesion substance (5 μg/ml) | | | | | | | | | | |
|---|---|---|---|---|---|---|---|---|---|---|---|---|
| | | BHK 21 | | | CEF | | B16F10 | CHO | | | baEC | |
| Lot No. | Amount (μg/ml) | FN | VN | FN | VN | FN | LN | LN | LN | FN | FN | ColI |
| 300(HA1-PPEADP) | 10 | + | | | | | | | | | | |
| | 100 | ++++ | | | | | | | | | | |
| 301(CH-PPEADP) | 10 | +++ | | +++ | | | | | | | | |
| | 100 | ++ | | ++ | | | | | | | | |
| 302(CS(S1)-PPEADP) | 10 | ++ | + | − | | | | | | | | |
| | 100 | − | − | − | | | | | | | | |
| 302-2(CS(S3)-PPEADP) | 10 | ++ | − | − | | − | − | − | + | − | | |
| | 100 | + | ± | − | | − | − | − | − | − | | |
| 302-3(CS(S6)-PPEADP) | 10 | ++ | + | − | | − | ± | − | − | | | |
| | 100 | − | + | − | | − | − | − | − | | | |
| 303(CS(W)-PPEADP) | 10 | ++ | − | − | | − | − | − | − | | | |
| | 100 | − | − | − | | − | − | − | − | | | |
| 304(DS-PPEADP) | 10 | +++ | | | | | | | | | | |
| | 100 | − | | | | | | | | | | |
| 305 (Hep-PPEADP) | 10 | ++++ | | | | | | | | | | |
| | 100 | +++ | | | | | | | | | | |
| 600(HA1-PPEADP) | 10 | +++ | | | | | | | | + | + | ± |
| | 100 | + | | | | | | | | ± | ± | ± |
| 601(CH-PPEADP) | 10 | ++ | | | | ± | | | | ± | ± | ± |
| | 100 | + | | | | + | | | | − | − | + |
| 602(CS(S1)-PPEADP) | 10 | − | | | | − | − | − | − | − | − | − |
| | 100 | − | | | | − | − | − | − | − | − | − |
| 602-2(CS(S3)-PPEADP) | 10 | − | | − | | − | − | − | | | | |
| | 100 | − | | − | | − | − | − | | | | |
| 702-2(CS(S3-P · S) | 10 | − | | | | | | | | | | |
| | 100 | − | | | | | | | | | | |
| 602-3(CS(S6)-PPEADP) | 10 | − | | − | | − | | | | | | |
| | 100 | − | | − | | ± | | | | | | |
| 604(DS-PPEADP) | 10 | ++ | | | | + | | | | | | |
| | 100 | + | | | | + | | | | | | |
| 605(Hep-PPEADP) | 10 | +++ | | | | − | | | | − | − | − |
| | 100 | + | | | | | | | | ± | ± | ± |
| 606(HS-PPEADP) | 10 | +++ | | | | | | | | | | |
| | 100 | + | | | | | | | | | | |
| 902-2(CS(S3)-GMS) | 10 | +++ | | +++ | | | | | | | | |
| | 100 | +++ | | ++ | | | | | | | | |
| 904(CS(S3)-GDS) | 10 | + | | − | | | | | | | | |
| | 100 | +++ | | − | | | | | | | | |
| 1000(HA1-PPEADP) | 10 | ++++ | | ++++ | | | | | | | | |
| | 100 | +++ | | ++ | | | | | | | | |
| 1001(CH-PPEADP) | 10 | +++ | + | − | | | | | | | | |
| | 100 | ++ | − | − | | | | | − | | | |
| 1002(CS(S1)-PPEADP) | 10 | − | | | | | | | | | | |
| | 100 | − | | | | | | | | | | |
| 1002-2(CS(S3)-PPEADP) | 10 | − | | | | | | | | | | |

TABLE O-continued

| | | \multicolumn{10}{c|}{Cells/cell adhesion substance (5 μg/ml)} |
| Lot No. | Amount (μg/ml) | BHK 21 | | CEF | | | B16F10 | | CHO | | baEC |
|---|---|---|---|---|---|---|---|---|---|---|---|
| | | FN | VN | FN | VN | FN | LN | LN | LN | FN | ColI |
| 1002-3(CS(S6)-PPEADP) | 100 | − | − | | | | | | − | | |
| | 10 | ++ | ++ | | | | | | | | |
| 1003(CS(W)-PPEADP) | 100 | + | + | | | | | | | | |
| | 10 | − | − | | | | | | | | |
| 1004(DS-PPEADP) | 100 | − | | − | | | | | | | |
| | 10 | ++++ | | − | | | | | | | |
| 1005 (Hep-PPEADP) | 100 | +++++ | | | | | | | | | |
| | 10 | +++ | | | | | | | | | |
| 1006(HS-PPEADP) | 100 | ++ | | | | | | | | | |
| | 10 | | | | | | | | | | |
| 1108(CPS(II)-PPEADP) | 100 | | | +++ | | | | | | | |
| | 10 | | | + | | | | | | | |
| HA1 | 100 | +++++ | +++++ | +++++ | +++++ | +++++ | +++++ | +++++ | +++ | | |
| HA5 | 100 | +++++ | +++++ | +++++ | +++++ | +++++ | +++++ | +++++ | +++++ | | |
| HA15 | 100 | +++++ | +++++ | +++++ | +++++ | +++++ | +++++ | +++++ | +++++ | | |
| CH | 100 | +++++ | +++++ | +++++ | +++++ | +++++ | +++++ | +++++ | +++++ | | |
| CS(S1) | 100 | +++++ | +++++ | +++++ | +++++ | +++++ | +++++ | +++++ | +++++ | | |
| CS(S3) | 100 | +++++ | +++++ | +++++ | +++++ | +++++ | +++++ | +++++ | +++++ | | |
| CS(S6) | 100 | +++++ | +++++ | +++++ | +++++ | +++++ | +++++ | +++++ | +++++ | | |
| CS(W) | 100 | +++++ | +++++ | +++++ | +++++ | +++++ | +++++ | +++++ | +++++ | | |
| DS | 100 | +++++ | +++++ | +++++ | +++++ | +++++ | +++++ | +++++ | +++++ | | |
| Hep | 100 | +++++ | +++++ | +++++ | +++++ | +++++ | +++++ | +++++ | +++++ | | |
| HS | 100 | +++++ | +++++ | +++++ | +++++ | +++++ | +++++ | +++++ | +++++ | | |
| KS | 100 | +++++ | +++++ | +++++ | +++++ | +++++ | +++++ | +++++ | +++++ | | |
| CPS(II) | 100 | +++++ | +++++ | +++++ | +++++ | +++++ | +++++ | +++++ | +++++ | | |
| PPEADP | 100 | +++++ | +++++ | +++++ | +++++ | +++++ | +++++ | +++++ | +++++ | | |

EXAMPLE 8

Effect of phospholipid-linked chondroitin sulfate C for inhibiting adhesion of highly metastatic cancer cells to extra-cellular matrix of blood vessel endothelial culture cells Mouse blood vessel endothelial cells were cultured in a 24-well incubation plate which had been coated with type I collagen so that the cells grew confluent. Single layer of the cells was treated with 0.5% Triton X-100 at room temperature for 30 minutes, and the thus-disintegrated fragments of the cell layer were washed with Dulbecco's PBS(+) buffer to obtain extra-cellular matrix of endothelial cells.

Separately, mouse-derived highly metastatic cancer cells (B16F10) cultured in a dish of 100 mm in diameter were treated with 5 ml of a trypsin solution (0.1 mg/ml PBS(−)) at 37° C. for 5 minutes. To the thus-treated cells was added 5 ml of 1 mg/ml solution of soy bean trypsin inhibitor in order to inactivate trypsin. Thereafter, the thus-separated cells were collected by centrifugation, washed twice with a phosphate buffer (PBS (−)) and then made into a single cell suspension (Hanks' BSS–20 mM HEPES, pH 7.4) with a density of $2 \times 10^5$ cells/ml.

The lot No. 602-2 phospholipid-linked chondroitin sulfate C (CS(S3)-PPEADP) and 500 μl of the thus-prepared single cell suspension of B16F10 ($1 \times 10^5$ cells) were transferred into each well of the aforementioned extra-cellular matrix-containing 24-well incubation plate and incubated statically at 37° C. for 1 hour in an incubator charged with 5% carbon dioxide.

The supernatant fluid in each well was took out gently, the residue was washed once gently with Hanks' buffer and both liquid portions were combined. Thereafter, the number of cells in the combined sample was counted using a cell counter (Coulter Electronics) to count cells which did not adhered to the extra-cellular matrix. A buffer solution containing no lot No. 602-2 compound (no addition) and a buffer containing free chondroitin sulfate C were used as controls.

Adhesion ratio of cells was calculated by subtracting the number of counted unadhered cells from the initially added total cells and dividing the remainder by the number of total cells. The results are shown in Table P.

TABLE P

| Sample | Amount added | Adhesion ratio |
| --- | --- | --- |
| No addition | — | 82.8% |
| Free chondroitin sulfate C | 50 μg | 82.6% |
| 602-2(CS(S3)-PPEADP) | 50 μg | 50.7% |

As is evident from the above results, the phospholipid-linked glycosaminoglycan of the present invention can inhibit adhesion of highly metastatic cancer cells to extra-cellular matrices of blood vessel endothelial cells, while free chondroitin sulfate C cannot exhibit such an effect.

EXAMPLE 9

Effect of phospholipid-linked chondroitin sulfate C for inhibiting metastasis of highly metastatic cancer cells Mouse-derived highly metastatic cancer cells (B16F10) cultured in a dish of 100 mm in diameter were treated with 5 ml of an EDTA solution (0.02%/PBS (−)) at 37° C. for 5 minutes, followed by cell separation by pipetting. The cells were collected by centrifugation, washed twice with a phosphate buffer (PBS (−)) and then made into a single cell suspension with a density of $1 \times 10^{-6}$ cells/ml. A 0.1 ml portion of this cell suspension ($10^5$ cells) was mixed with 0.1 ml of a PBS solution of the lot No. 602-2 (CS(S3)-PPEADP) phospholipid-linked glycosaminoglycan (0.1 mg, 1 mg or 5 mg/0.1 ml) and the resulting mixture was administered to C57BL/6 mice through tail vein. Thoracotomy was carried out 2 weeks after the administration to count the number of melanoma colonies metastasized to the surface of the lungs. A buffer solution containing no lot No. 602-2 (CS(S3)-PPEADP) compound (no addition) and a buffer containing free chondroitin sulfate C were used as controls.

Table Q shows the results of counting colonies metastasized to the surface of the lungs per mouse.

TABLE Q

| Sample | Dose (mg/mouse) | Colonies (numbers/mouse) |
| --- | --- | --- |
| No addition | — | 49.9 ± 32.3 |
| Free chondroitin sulfate C | 5 mg | 24.0 ± 8.0 |
| 602-2(CS(S3)-PPEADP) | 0.1 mg | 47.2 ± 28.1 |
|  | 1 ml | 22.0 ± 14.8 |
|  | 5 mg | 4.0 ± 3.5 |

Metastasis of cancer cells was inhibited as the dose of the phospholipid-linked chondroitin sulfate C increased. As is evident from these results, the phospholipid-linked glycosaminoglycan of the present invention can inhibit metastasis of highly metastatic cancer cells. Free chondroitin sulfate C also inhibited the metastasis, but its effect was inferior to that of the phospholipid-linked chondroitin sulfate C (p<0.001).

Industrial Applicability

The phospholipid- or lipid-linked glycosaminoglycans or their salts of the present invention which has cell adhesion-inhibitory activity and has no toxicity are useful as metastasis inhibitors.

What is claimed is:

1. A process for producing a phospholipid- or lipid-linked glycosaminoglycan represented by the following formula (VI),

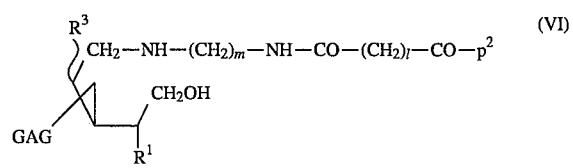

or a salt thereof, which comprises the steps of:

(a) reacting an aldehyde compound represented by the following formula (II-3)

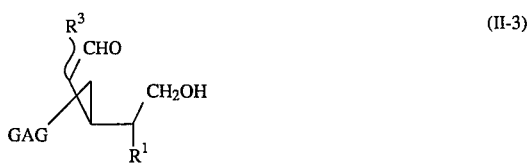

with an alkylene diamine thereby obtaining a compound of formula (16)

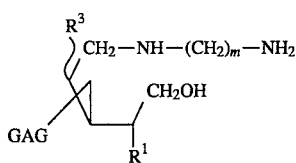

wherein
(1) $R^1$ is —NHCOCH$_3$ and $R^3$ is an —OH group when GAG is a glycosaminoglycan residue of hyaluronic acid or chondroitin, wherein the reducing terminal hexosamine thereof has been removed,
(2) $R^1$ is —NHCOCH$_3$ and $R^3$ is an —OSO$_3$H group when GAG is a glycosaminoglycan residue of chondroitin sulfate A or K, chondroitin polysulfate or dermatan sulfate, wherein the reducing terminal hexosamine moiety thereof has been removed, and
(3) each of $R^1$ and $R^3$ is an —OH group when GAG is a glycosaminoglycan residue of keratan sulfate or keratan polysulfate, wherein the reducing terminal galactose moiety thereof has been removed, and m is an integer of 1 to 8 and l is an integer of 1 to 10;

(b) separately reacting a phospholipid or lipid ($P^2$), wherein $P^2$ is a phospholipid or a lipid represented by the following formulae:

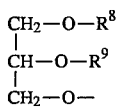     (X)

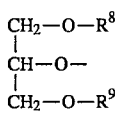     (XI)

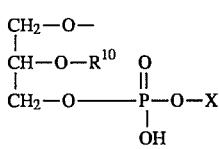     (XII)

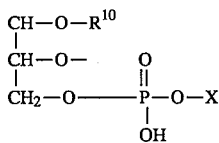     (XIII)

wherein $R^8$ is hydrogen, $R^9$ is an alkyl group, $R^{10}$ is —CH=CHR$^6$ or —COR$^7$, wherein each of $R^6$ and $R^7$ is a $C_{6-24}$ alkyl group, m is an integer of 1 to 8 and l is an integer of 1 to 10, and X is —CH$_2$CH$_2$N$^+$(CH$_3$)$_3$ or an inositol residue, and GAG is a glycosaminoglycan residue of hyaluronic acid, chondroitin, chondroitin sulfate A, chondroitin sulfate K, chondroitin polysulfate, dermatan sulfate, keratan sulfate or keratan polysulfate, with a dicarboxylic acid or a dicarboxylic acid anhydride to obtain a phospholipid or lipid having a carboxyl group; and (c) reacting a primary amino group in the resulting compound of formula (16) with the resulting carboxyl group in the phospholipid or lipid.

2. A phospholipid-linked glycosaminoglycan, or a salt thereof, in which a primary amino group of a phospholipid is linked to a carbonyl group of a reducing terminal moiety of a glycosaminoglycan through an amido bond, said phospholipid-linked glycosaminoglycan being represented by the following formulae:

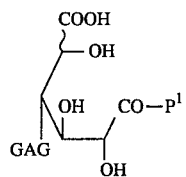     IV-(1)

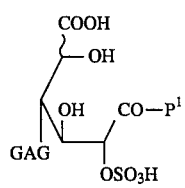     IV-(2)

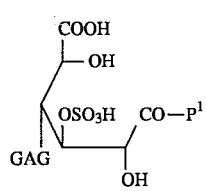     IV-(3)

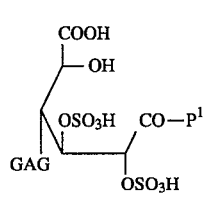     IV-(4)-a

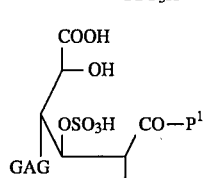     IV-(4)-b

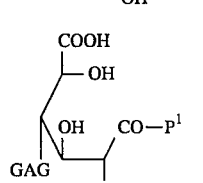     IV-(4)-c

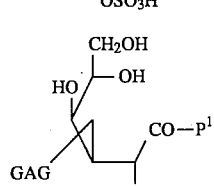     IV-(5)

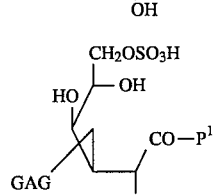     IV-(6)

-continued

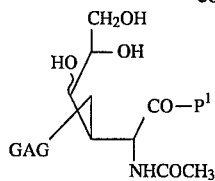 IV-(7)

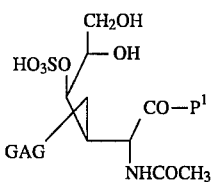 IV-(8)

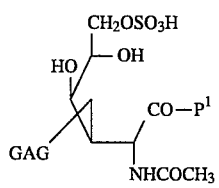 IV-(9)

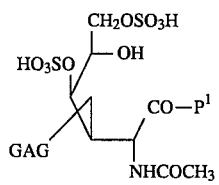 IV-(10)

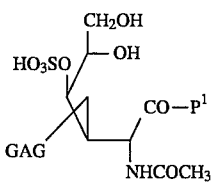 IV-(11)-a

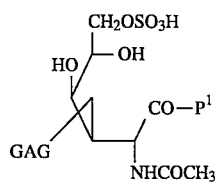 IV-(11)-b

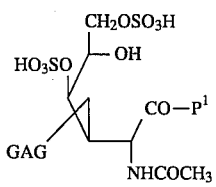 IV-(11)-c

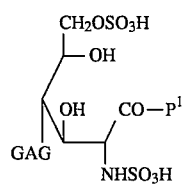 IV-(12)

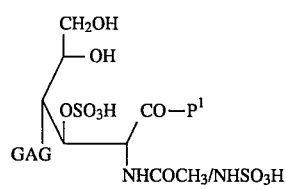 IV-(13)-a

-continued

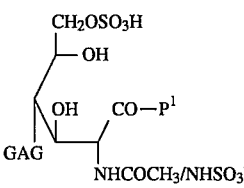 IV-(13)-b

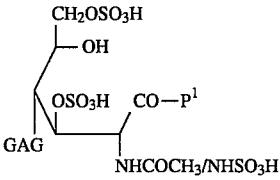 IV-(13)-c

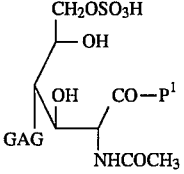 IV-(14)-b wherein $P^1$ is a phospholipid represented by the formula (IX):

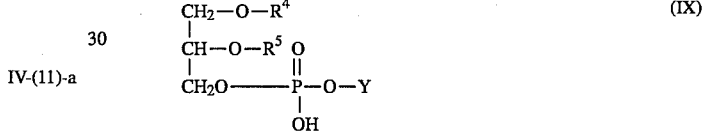 (IX)

wherein each of $R^4$ and $R^5$ is hydrogen, —CH=CHR$^6$ or —COR$^7$, wherein each of $R^6$ and $R^7$ is a $C_{6-24}$ alkyl group, and Y is —CH$_2$CH$_2$NH— or

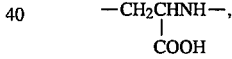

and GAG is a glycosaminoglycan residue of hyaluronic acid, chondroitin, chondroitin sulfate A, C, D, E or K, chondroitin polysulfate, dermatan sulfate, heparin, heparan sulfate, keratan sulfate or keratan polysulfate, wherein the reducing terminal group has been removed.

3. The phospholipid-linked glycosaminoglycan according to claim 2, wherein said glycosaminoglycan is selected from the group consisting of chondroitin sulfate A, C, D, E or K, and dermatan sulfate, and said phospholipid is phosphatidylethanolamine or phosphatidylserine.

4. A phospholipid or lipid-linked glycosaminoglycan, or a salt thereof, in which an oxygen atom of a hydroxyl group of a phospholipid- or a lipid is linked to a terminal carbonyl group of a group represented by —NH—(CH$_2$)$_m$—NHCO—(CH$_2$)$_l$—CO— through an ester bond, and an aldehyde residue of a reducing terminal moiety of a glycosaminoglycan is linked to a terminal —NH group of a group represented by —NH—(CH$_2$)$_m$—NHCO—(CH$_2$)$_l$—CO— through a CH$_2$NH bond, said phospholipid- or lipid-linked glycosaminoglycan being represented by the following formulae:

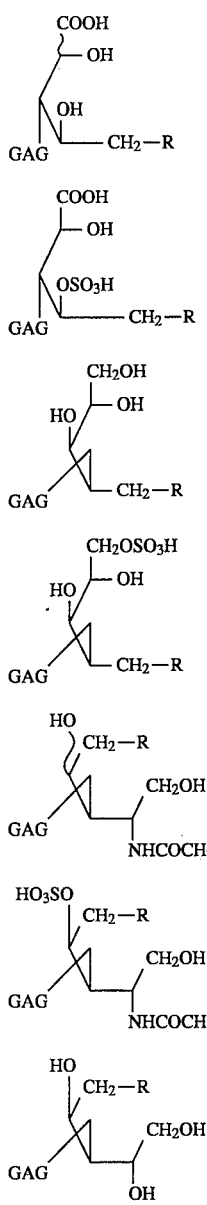

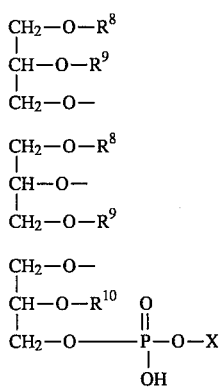

wherein R represents —NH—(CH$_2$)$_m$—NHCO—(CH$_2$)$_l$—CO—P$^2$, wherein P$^2$ is a phospholipid or a lipid represented by the following formulae:

$$\begin{array}{l} CH_2-O-R^8 \\ CH-O-R^9 \\ CH_2-O- \end{array} \quad (X)$$

$$\begin{array}{l} CH_2-O-R^8 \\ CH-O- \\ CH_2-O-R^9 \end{array} \quad (XI)$$

$$\begin{array}{l} CH_2-O- \\ CH-O-R^{10} \quad O \\ CH_2-O\!-\!\!-\!\!-P-O-X \\ \qquad\qquad\quad OH \end{array} \quad (XII)$$

$$\begin{array}{l} CH-O-R^{10} \\ CH-O- \quad O \\ CH_2-O\!-\!\!-\!\!-P-O-X \\ \qquad\qquad\quad OH \end{array} \quad (XIII)$$

wherein R$^8$ is hydrogen, R$^9$ is an alkyl group, R$^{10}$ is —CH=CHR$^6$ or —COR$^7$, wherein each of R$^6$ and R$^7$ is a C$_{6-24}$ alkyl group, m is an integer of 1 to 8 and l is an integer of 1 to 10, and X is —CH$_2$CH$_2$N$^+$(CH$_3$)$_3$ or an inositol residue, and GAG is a glycosaminoglycan residue of hyaluronic acid, chondroitin, chondroitin sulfate A, chondroitin sulfate C, chondroitin sulfate D, chondroitin sulfate E, chondroitin sulfate K, chondroitin polysulfate, dermatan sulfate, heparin, heparan sulfate, keratan sulfate or keratan polysulfate.

5. A phospholipid- or lipid-linked glycosaminoglycan, or a salt thereof, in which an oxygen atom of a hydroxyl group of a phospholipid or a lipid is linked to a terminal carbonyl group of a group represented by —NH—(CH$_2$)$_m$—NHCO—(CH$_2$)$_l$—CO— through an ester bond, and a carbonyl group of a reducing terminal moiety of a glycosaminoglycan is linked to a terminal —NH group of a group represented by —NH—(CH$_2$)$_m$—NHCO—(CH$_2$)$_l$—CO— through an amido bond, said phospholipid- or lipid-linked glycosaminoglycan being represented by the following formulae:

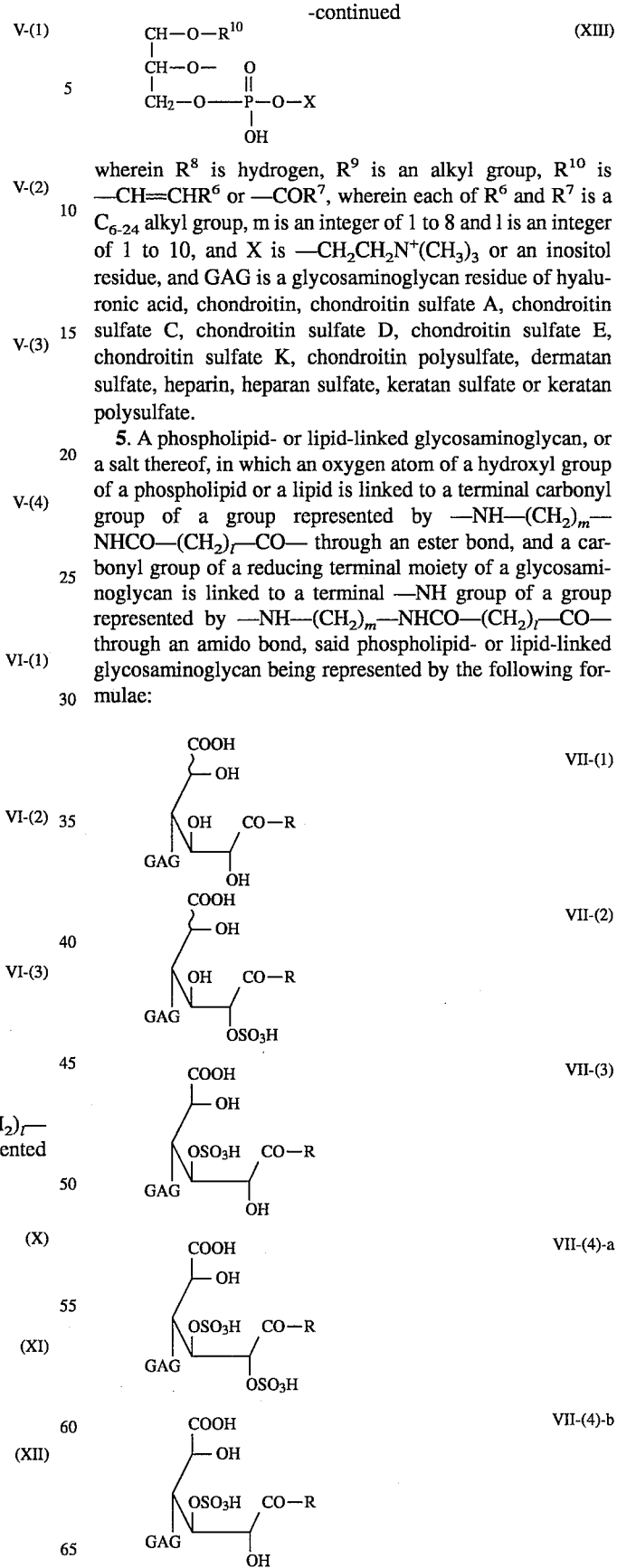

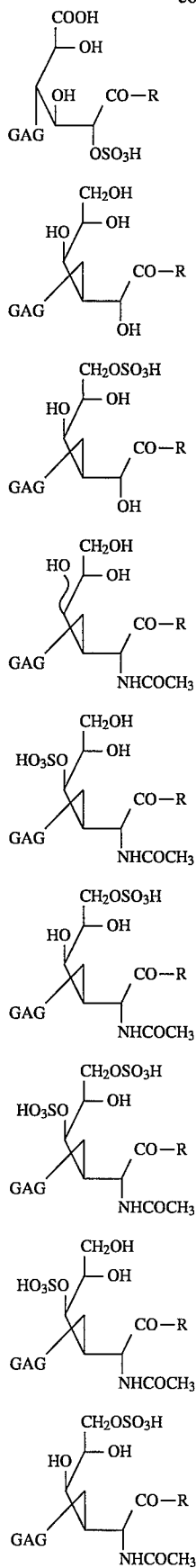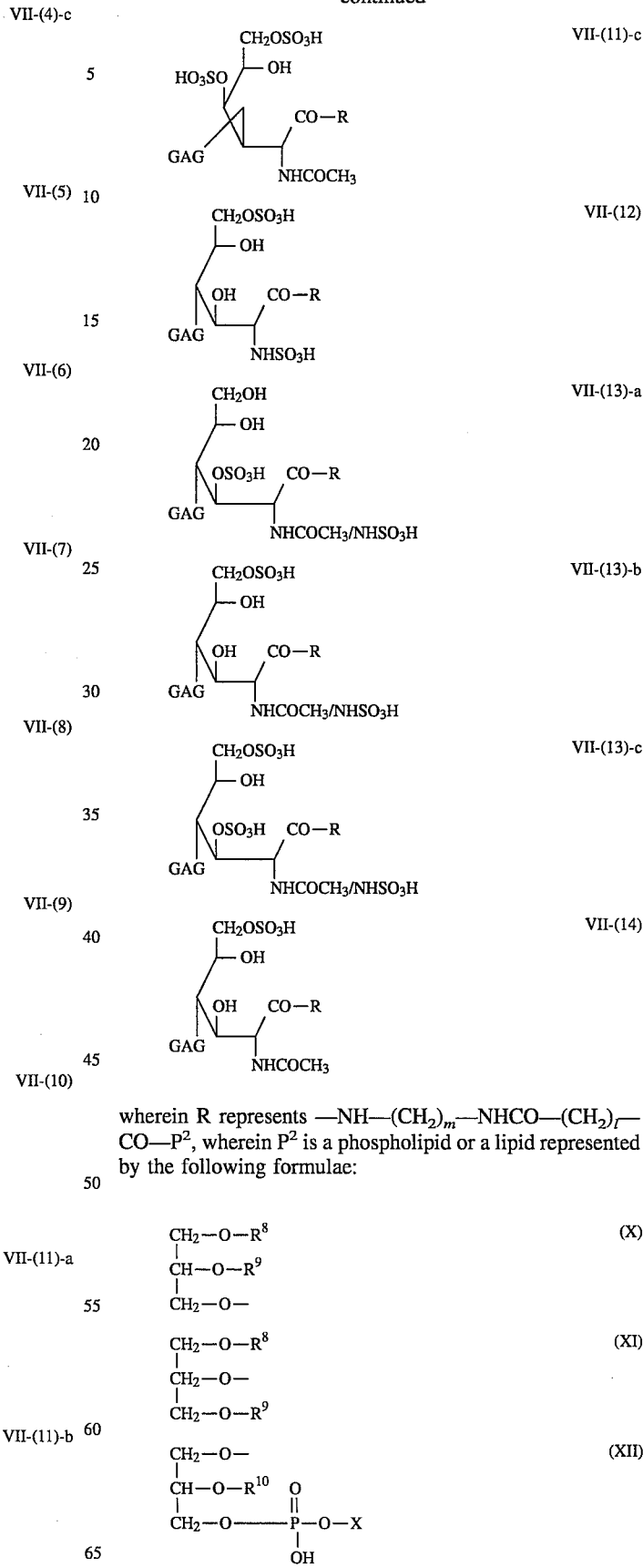
wherein R represents $-NH-(CH_2)_m-NHCO-(CH_2)_l-CO-P^2$, wherein $P^2$ is a phospholipid or a lipid represented by the following formulae:

-continued

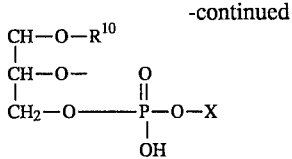 (XIII)

wherein $R^8$ is hydrogen, $R^9$ is an alkyl group, $R^{10}$ is —CH=CHR$^6$ or —COR$^7$, wherein each of $R^6$ and $R^7$ is a $C_{6-24}$ alkyl group, m is an integer of 1 to 10, and X is —CH$_2$CH$_2$N$^+$(CH$_3$) or an inositol residue, and GAG is a glycosaminoglycan residue of hyaluronic acid, chondroitin, chondroitin sulfate A, chondroitin sulfate C, chondroitin sulfate D, chondroitin sulfate E, chondroitin sulfate K, chondroitin polysulfate, dermatan sulfate, heparin, heparan sulfate, keratan sulfate or keratan polysulfate.

6. A phospholipid-linked glycosaminoglycan, or a salt thereof, in which a primary amino group of a phospholipid is linked to a carboxyl group of a uronic acid moiety of a glycosaminoglycan, said phospholipid-linked glycosaminoglycan being represented by the following formula:

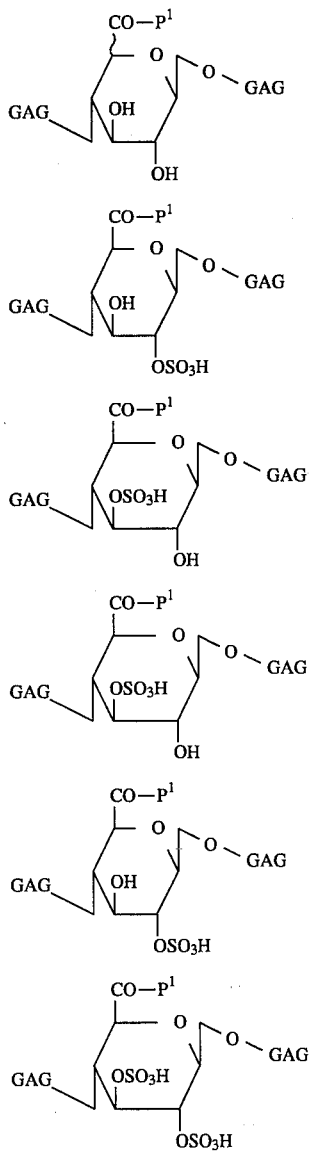

VIII-(1)
VIII-(2)
VIII-(3)
VIII-(4)-a
VIII-(4)-b
VIII-(4)-c

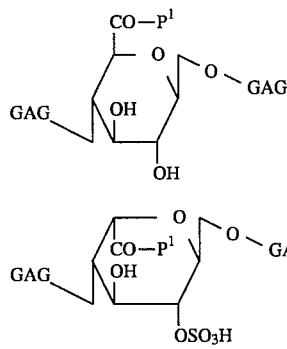

VIII-(5)-a
VIII-(5)-b wherein $P^1$ is a phospholipid represented by the formula (IX):

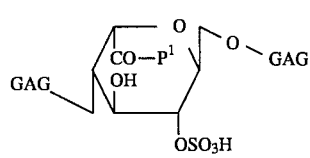 (IX)

wherein each of $R^4$ and $R^5$ is hydrogen, —CH=CHR$^6$ or —COR$^7$, wherein each of $R^6$ and $R^7$ is a $C_{6-24}$ alkyl group, and Y is —CH$_2$CH$_2$NH— or

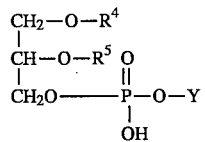

and GAG is a glycosaminoglycan residue of hyaluronic acid, chondroitin, chondroitin sulfate A, C, D, E or K, chondroitin polysulfate, dermatan sulfate, heparin or heparan sulfate, wherein the reducing terminal group has been removed.

7. A method of inhibiting adhesion of animal cells to an adhesion protein, which comprises incubating the animal cells in the presence of a phospholipid-linked glycosaminoglycan prepared according to claim 2.

8. A method of inhibiting adhesion of animal cells to an adhesion protein, which comprises incubating the animal cells in the presence of a phospholipid- or lipid-linked glycosaminoglycan prepared according to claim 4.

9. A method of inhibiting adhesion of animal cells to an adhesion protein, which comprises incubating the animal cells in the presence of a phospholipid- or lipid-linked glycosaminoglycan prepared according to claim 5.

10. A method of inhibiting adhesion of animal cells to an adhesion protein, which comprises incubating the animal cells in the presence of a phospholipid-linked glycosaminoglycan prepared according to claim 6.

11. A process for producing a phospholipid-linked glycosaminoglycan in which a primary amino group of a phospholipid is linked to a carbonyl group of a reducing terminal moiety of a glycosaminoglycan through an amido bond, or a salt thereof, which comprises the steps of:

(a) oxidizing and cleaving the reducing terminal group of a glycosaminoglycan thereby obtaining an oxidized product;

(b) preparing from the resulting oxidized product a lactone; and (c) reacting the resulting lactone with a primary amino group of a phospholipid to obtain said phospholipid-linked glycosaminoglycan, wherein the phospholipid is represented by the formula (IX):

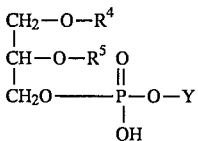

wherein each of $R^4$ and $R^5$ is hydrogen, —CH=CHR$^6$ or —COR$^7$, wherein each of $R^6$ and $R^7$ is a $C_{6-24}$ alkyl group, and Y is —CH$_2$CH$_2$NH— or

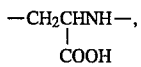

and said glycosaminoglycan is selected from the group consisting of hyaluronic acid, chondroitin, chondroitin sulfate A, C, D, E or K, chondroitin polysulfate, dermatan sulfate, heparin, heparan sulfate, keratan sulfate and keratan polysulfate.

12. A process for producing a phospholipid- or lipid-linked glycosaminoglycan in which an oxygen atom of a hydroxy group of a phospholipid or a lipid is linked to a carbonyl group of a group represented by —NH—(CH$_2$)$_m$—NHCO—(CH$_2$)$_l$—CO—, wherein m is an integer of 1 to 8 and l is an integer of 1 to 10, through an ester bond, and an aldehyde residue of a reducing terminal moiety of a glycosaminoglycan is linked to a —NH group of a group represented by —NH—(CH$_2$)$_m$—NHCO—(CH$_2$)$_l$—CO—, wherein m and l are as defined above, through a CH$_2$NH bond, or a salt thereof, which comprises the steps of:

(a) reacting an aldehyde residue of a reducing terminal moiety of a glycosaminoglycan with an alkylene diamine;

(b) separately reacting a phospholipid or lipid with a dicarboxylic acid or a dicarboxylic acid anhydride to obtain a phospholipid or lipid having a carboxyl group; and (c) reacting a primary amino group in the resulting compound obtained in the above step (a) with the resulting carboxyl group in the phospholipid or lipid obtained in the above step (b), wherein said lipid or phospholipid is represented by the formulae:

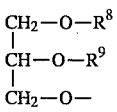

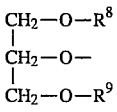

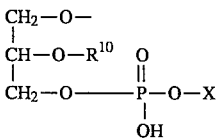

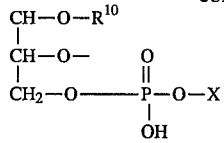

wherein $R^8$ is hydrogen, $R^9$ is an alkyl group, $R^{10}$ is —CH=CHR$_6$ or —COR$^7$, wherein each of $R^6$ and $R^7$ is a $C_{6-24}$ alkyl group, and X is —CH$_2$CH$_2$N$^+$(CH$_3$)$_3$ or an inositol residue, and said glycosaminoglycan is selected from the group consisting of hyaluronic acid, chondroitin, chondroitin sulfate A, C, D, E or K, chondroitin polysulfate, dermatan sulfate, heparin, heparan sulfate, keratan sulfate and keratan polysulfate.

13. A process for producing a phospholipid- or lipid-linked glycosaminoglycan in which an oxygen atom of a hydroxyl group of a phospholipid or a lipid is linked to a carbonyl group of a group represented by —NH—(CH$_2$)$_m$—NHCO—(CH$_2$)$_l$—CO—, wherein m is an integer of 1 to 8 and l is an integer of 1 to 10, through an ester bond, and a carbonyl group of a reducing terminal moiety of a glycosaminoglycan is linked to a —NH group of a group represented by —NH—(CH$_2$)$_m$—NHCO—(CH$_2$)$_l$—CO—, wherein m and l are as defined above, through an amido bond, or a salt thereof, which comprises the steps of:

(a) reacting a carbonyl group of a reducing terminal moiety of a glycosaminoglycan with an alkylene diamine;

(b) separately reacting a phospholipid or lipid with a dicarboxylic acid or a dicarboxylic acid anhydride to obtain a phospholipid or lipid having a carboxyl group; and (c) reacting a primary amino group in the resulting compound obtained in the above step (a) with the resulting carboxyl group in the phospholipid or lipid obtained in the above step (b), wherein said lipid or phospholipid is represented by the formulae:

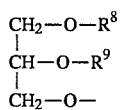

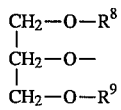

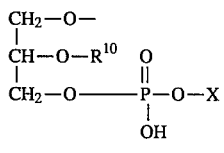

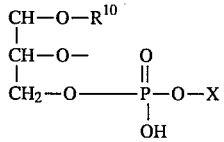

wherein $R^8$ is hydrogen, $R^9$ is an alkyl group, $R^{10}$ is —CH=CHR$^6$ or —COR$^7$, wherein each of $R^6$ and $R^7$ is a $C_{6-24}$ alkyl group, and X is —CH$_2$CH$_2$N$^+$(CH$_3$)$_3$ or an inositol residue, and said glycosaminoglycan is selected from the group consisting of hyaluronic acid, chondroitin, chondroitin sulfate A, C, D, E or K, chondroitin polysulfate, dermatan sulfate, heparin, heparan sulfate, keratan sulfate and keratan polysulfate.

14. A process for producing a phospholipid-linked glycosaminoglycan in which a primary amino group of a phospholipid is linked to a carboxyl group of a uronic acid moiety of a glycosaminoglycan, or a salt thereof, which comprises reacting a primary amino group of a phospholipid, in the presence of a condensing agent, with a carboxyl group of a glycosaminoglycan thereby obtaining said phospholipid-linked glycosaminoglycan, wherein the phospholipid is represented by the formula (IX):

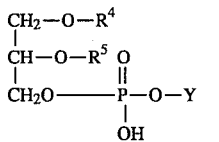
(IX)

wherein each of $R^4$ and $R^5$ is hydrogen, —CH=$CHR^6$ or —$COR^7$, wherein each of $R^6$ and $R^7$ is a $C_{6-24}$ alkyl group, and Y is —$CH_2CH_2NH$— or

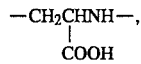

and said glycosaminoglycan is selected from the group consisting of hyaluronic acid, chondroitin, chondroitin sulfate A, C, D, E or K, chondroitin polysulfate, dermatan sulfate, heparin and heparan sulfate.

15. A process for producing a phospholipid-linked glycosaminoglycan in which a primary amino group of a phospholipid is linked to a carboxyl group of a uronic acid moiety of a glycosaminoglycan, or a salt thereof, which comprises the steps of:

(a) activating a carboxyl group of a glycosaminoglycan; and (b) reacting the resulting activated carboxyl group with a primary amino group of a phospholipid to obtain said phospholipid-linked glycosaminoglycan, wherein the phospholipid is represented by the formula (IX):

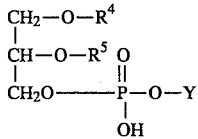
(IX)

wherein each of $R^4$ and $R^5$ is hydrogen, —CH=$CHR^6$ or —$COR^7$, wherein each of $R^6$ and $R^7$ is a $C_{6-24}$ alkyl group, and Y is —$CH_2CH_2NH$— or

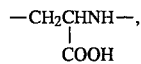

and said glycosaminoglycan is selected from the group consisting of hyaluronic acid, chondroitin, chondroitin sulfate A, C, D, E or K, chondroitin polysulfate, dermatan sulfate, heparin and heparan sulfate.

16. A phospholipid-linked glycosaminoglycan in which a primary amino group of a phospholipid is linked to a carbonyl group of a reducing terminal moiety of a glycosaminoglycan through an amido bond, or a salt thereof, which is obtained by a process comprising the steps of:

(a) oxidizing and cleaving the reducing terminal group of a glycosaminoglycan thereby obtaining an oxidized product;

(b) preparing from the resulting oxidized product a lactone; and (c) reacting the resulting lactone with a primary amino group of a phospholipid to obtain said phospholipid-linked glycosaminoglycan, wherein the phospholipid is represented by the formula (IX):

(IX)

wherein each of $R^4$ and $R^5$ is hydrogen, —CH=$CHR^6$ or —$COR^7$, wherein each of $R^6$ and $R^7$ is a $C_{6-24}$ alkyl group, and Y is —$CH_2CH_2NH$— or

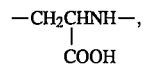

and said glycosaminoglycan is selected from the group consisting of hyaluronic acid, chondroitin, chondroitin sulfate A, C, D, E or K, chondroitin polysulfate, dermatan sulfate, heparin, heparan sulfate, keratan sulfate and keratan polysulfate.

17. A phospholipid- or lipid-linked glycosaminoglycan in which an oxygen atom of a hydroxy group of a phospholipid or a lipids is linked to a carbonyl group of a group represented by —NH—$(CH_2)_m$—NHCO—$(CH_2)_l$—CO—, wherein m is an integer of 1 to 8 and l is an integer of 1 to 10, through an ester bond and a carbonyl group of a reducing terminal moiety of a glycosaminoglycan is linked to a —NH group of a group represented by —NH—$(CH_2)_m$—NHCO—$(CH_2)_l$—CO—, wherein m and l are as defined above, through an amido bond, or a salt thereof, which is obtained by a process comprising the steps of:

(a) reacting a carbonyl group of a reducing terminal moiety of a glycosaminoglycan with an alkylene diamine;

(b) separately reacting a phospholipid or lipid with a dicarboxylic acid or a dicarboxylic acid anhydride to obtain a phospholipid or lipid having a carboxyl group; and (c) reacting a primary amino group in the resulting compound obtained in the above step (a) with the resulting carboxyl group in the phospholipid or lipid obtained in the above step (b), wherein said lipid or phospholipid is represented by the formulae:

(X)

(XI)

-continued

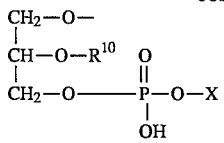
(XII)

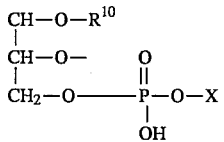
(XIII)

wherein $R^8$ is hydrogen, $R^9$ is an alkyl group, $R^{10}$ is —CH=CHR$^6$ or —COR$^7$, wherein each of $R^6$ and $R^7$ is a $C_{6-24}$ alkyl group and X is —CH$_2$CH$_2$N$^+$(CH$_3$)$_3$ or an inositol residue, and said glycosaminoglycan is selected from the group consisting of hyaluronic acid, chondroitin, chondroitin sulfate A, C, D, E or K, chondroitin polysulfate, dermatan sulfate, heparin, heparan sulfate, keratan sulfate and keratan polysulfate.

* * * * *

UNITED STATES PATENT AND TRADEMARK OFFICE
CERTIFICATE OF CORRECTION

PATENT NO. : 5,464,942
DATED : November 7, 1995
INVENTOR(S) : Katsukiyo Sakural, et. al.

It is certified that error appears in the above-identified patent and that said Letters Patent is hereby corrected as shown below:

Column 69, (Claim 5), line 10, "m is an integer of 1 to 10" should be -- m is an integer of 1 to 8, $\ell$ is an integer of 1 to 10 --.

Signed and Sealed this

Sixteenth Day of December, 1997

Attest:

BRUCE LEHMAN

Attesting Officer

Commissioner of Patents and Trademarks